US007595056B1

(12) United States Patent
Mendis-Handagama

(10) Patent No.: US 7,595,056 B1
(45) Date of Patent: Sep. 29, 2009

(54) METHODS OF REJUVENATING LEYDIG CELLS AND ENHANCING TESTOSTERONE PRODUCTION IN A MALE SUBJECT

(75) Inventor: S. M. L. Chamindrani Mendis-Handagama, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 411 days.

(21) Appl. No.: 10/449,634

(22) Filed: May 30, 2003

Related U.S. Application Data

(60) Provisional application No. 60/384,249, filed on May 30, 2002.

(51) Int. Cl.
*A61K 39/00* (2006.01)
*A01N 37/18* (2006.01)

(52) U.S. Cl. ........................................ 424/198.1; 514/2

(58) Field of Classification Search ........................ None
See application file for complete search history.

(56) References Cited

OTHER PUBLICATIONS

Elmlinger et al. 2003 Clin Chem Lab Med. 41:934-941.*
Antony et al. 1995. J Endocrin. 144:293-300.*
Mendis-Handagama et al. 2001. J Andrology 22, Supplement. p. 174, abstract 080.*
St. Germain DL. 2001. in Endocrinology, 4th ed. vol. 2, pp. 13230-1326.*
Mooradian 1995. Clinics in Geriatic Medicine 11(2):159-169.*
Jarow et al. 1994. J of Andrology. 15:456-461.*
Zirken et al. 2000. Biology of Reproduction 63:977-981.*
Hermann et al. (1999. Experimental Gerontology 34:923-933.*
Murray et al 1993. World J Urol. 11:37-40.*
Lipson et al 1979. J of Nuclear Medicine 20:1124-1130.*
Briblescas 2005. Am J. Phys Anthrop. 127:114-121.*
Chamindrani Mendis-Handagama et al. *Differentiation of the auault Leydig Cell population in the postnatal testis. Biology of Reproduction*, vol. 65, (2001), pp. 660-671.
Mariotti et al. *The aging thyroid. Endocrine Reviews*, vol. 16, No. 6, (1995), pp. 686-715.
Mulligan et al. *Male Menapause. Drugs of Today*, vol. 34, No. 5, (1998), pp. 455-461.
Urban et al. *Attenuated release of biologically active luteinizing hormone in healthy aging men. Journal of Clinical Investigation*, vol. 81, (1988), pp. 1020-1029.
Veldhuis et al. *Differential resposes of biologically active luteinizing hormone secretion in older versus young men to interruption of androgen negative feedback. Journal of Clinical Endocrinology and Metabolism*, vol. 79, No. 6, (1994), pp. 1763-1770.
Veldhuis et al. *Pathophysiological features of the pulsatile secretion of biologically active luteinizing hormone in man. Journal of Steroid Biochemistry and Molecular Biology*, vol. 33, No. 4B, (1989), pp. 739-749.

Weissel, Michael. *Disturbances of thyroid function in the elderly. Wien Klin Wochenschr*, vol. 118, Nos. 1-2, (2006), pp. 16-20.
Kim et al., "Changes in the Testis Interstitium of Brown Norway Rats with Aging and Effects of Luteinizing and Thyroid Hormones on the Aged Testes in Enhancing the Steroidogenic Potential," Biology of Reproduction, vol. 66 pp. 1359-1366 (2002).
Bonavera et al., "In the Male Brown-Norway (BN) Male Rat, Reproductive Aging Is Associated With Decreased LH-Pulse Amplitude and Area," Journal of Andrology, vol. 18. No. 4, pp. 359-365 (Jul./Aug. 1997).
Chen et al., "Dibutyryl Cyclic Adenosine Monophosphate Restores the Ability of Aged Leydig Cells to Produce Testosterone at the High Levels Characteristic of Young Cells," Endocrinology, vol. 145, No. 10, pp. 4441-4446 (2004).
Gruenewald et al., "The Brown Norway Rat as a Model of Male Reproductive Aging: Evidence for Both Primary and Secondary Testicular Failure," J. Gerontol., vol. 49, No. 2, B42-50 (1994). Abstract.
Matsumoto et al., "Aging and the neuroendocrine regulation of reproduction and body weight," Experimental Gerontology, vol. 35, pp. 1251-1265 (2000).
Midzak et al., "Leydig cell aging and the mechanisms of reduced testosterone synthesis," Molecular and Cellular Endocrinology, In Press, Corrected Proof, Available online Aug. 5, 2008 (Sep. 17, 2008).
Syed et al., "Selective Loss of Sertoli Cell and Germ Cell Function Leads to a Disruption in Sertoli Cell-Germ Cell Communication During Aging in the Brown Norway Rat," Biology of Reproduction, vol. 64, pp. 107-112 (2001).
Schoenfeld et al., "Continuously Proliferative Stem Germ Cells Partially Repopulate the Aged, Atrophic Rat Testis after Gonadotropin-Releasing Hormone Agonist Therapy," Biology of Reproduction, vol. 64, pp. 1273-1282 (2001).
Takahashi, "Age Attenuates Testosterone Secretion Driven by Amplitude-Varying Pulses of Recombinant Human Luteinizing Hormone during Acute Gonadotrope Inhibition in Healthy Men," The Journal of Clinical Endocrinology & Metabolism, vol. 92, No. 9, pp. 3626-3632 (2007).
Veldhuis et al., "The Aging Male Hypothalamic-Pituitary-Gonadal Axis: Pulsatility and feedback," Molecular and Cellular Endocrinology, In Press, Accepted Manuscript, Available online Sep. 17, 2008.
Wang et al., "Reproductive Aging in the Male Brown-Norway Rat: A Model for the Human," Endocrinology, vol. 133, No. 6, pp. 2773-2781 (1993).

* cited by examiner

*Primary Examiner*—Manjunath N Rao
*Assistant Examiner*—Shulamith H Shafer
(74) *Attorney, Agent, or Firm*—Jenkins, Wilson, Taylor & Hunt, P.A.

(57) ABSTRACT

A method of rejuvenating Leydig cells in a subject having Leydig cells is disclosed. Rejuvenation of Leydig cells is accomplished, in one embodiment, by coadministering TH and LH to a subject. Rejuvenating Leydig cells can enhance serum testosterone levels and can have other desirable effects as well. The presently claimed subject matter also encompasses methods relating to the treatment of andropause and the elevation of serum testosterone levels.

2 Claims, 7 Drawing Sheets

SEQUENCE LISTING

```
<160> NUMBER OF SEQ ID NOS: 6

<210> SEQ ID NO 1
<211> LENGTH: 1798
<212> TYPE: DNA
<213> ORGANISM: Rattus norvegicus
<220> FEATURE:
<221> NAME/KEY: CDS
<222> LOCATION: (802)..(816)
<220> FEATURE:
<221> NAME/KEY: CDS
<222> LOCATION: (1062)..(1229)
<220> FEATURE:
<221> NAME/KEY: CDS
<222> LOCATION: (1455)..(1694)
<300> PUBLICATION INFORMATION:
<301> AUTHORS: Chin et al.
<302> TITLE: Nucleotide sequence of the cDNA encoding the precursor of
       the beta subunit of rat lutropin
<303> JOURNAL: Proc. Natl. Acad. Sci. U.S.A.
<304> VOLUME: 80
<305> ISSUE: 15
<306> PAGES: 4649-4653
<307> DATE: 1983
<308> DATABASE ACCESSION NUMBER: NCBI/J00749
<309> DATABASE ENTRY DATE: 1996-04-09
<313> RELEVANT RESIDUES: (1)..(1798)

<400> SEQUENCE: 1
ccatcgcaac cgatcgtgcc atacttggga ggccctgcct ctgacaccgg ggtcctacgg     60
acccccgatg cacccgttct gtaggatgga ccgcatttgc ctagtagacg cacccctgggg   120 aggcctccac cggaatccag tgccaggcat ctacagtgta ccgaaggcct actgcactgt    180
gaattcccgc tatgggagtg ctaggaggga gctggtgtga gcgtgtgaag cccacccaca    240
acgcaaactc caacattaga cttgtgggca ggccaaccca gacacacccc ttcctcacag    300
aggttcctcc aggcggagtt tactgatcaa gaagttttat agctgaaacc acaccatt      360 ttggacccaa tccaggcatc ctgattaggg ggctgggcga ggggcggcgc ccacctctgg    420
ttgtgtttaa agcaaatttg agccactgtc agaaccgaac accgaagctg tgccctccat    480
tcagttgtac tcaaccatcg gagtgggtct gactgaagtt catccagcat cctagggcca    540
```

```
gctagcagcc tgcagagttc tccccttac ctgttccctg tgttcccaat gtcagttaag      600
ctcaggcacc tgggctgagt gtgaggccaa ttcactgaga cactggagct tggtccttgg      660
tcctttctga ccttgtctgt ctcgccccca aagagattag tgtctaggtt acccaggcct      720
gtagcctctg cttagtggcc ttgccacccc cacaacccgc aggtataaag ccaagtgccc      780
aaggtaggga aggtatcaag a atg gag agg ctc cag gtaagatggt agggcccaag      836
              Met Glu Arg Leu Gln
                1           5 gtacctcccg attctagcag acccatcga tggacagcct tgtgacctag gggttggagg      896
atggagagga aggggggctcc taactggtgg acgtcaagta agagaaatag atttgatggc      956
gggtgatggg tcttgatgga cagtttctct attatactga gcggctccag aacctggaat     1016
gcaaaagcca ggtcagggat agaatggaca ctggctatgt cccag ggg ctg ctg ctg      1073
                                                Gly Leu Leu Leu tgg ctg ctg ctg agc cca agt gtg gtg tgg gcc tcc agg ggc ccc ctt      1121
Trp Leu Leu Leu Ser Pro Ser Val Val Trp Ala Ser Arg Gly Pro Leu
 10              15                  20                  25 cgg cca ctg tgc cgg cct gtc aac gca acc ctg gct gca gag aat gag      1169
Arg Pro Leu Cys Arg Pro Val Asn Ala Thr Leu Ala Ala Glu Asn Glu
             30                  35                  40 ttc tgc cca gtc tgc atc acc ttc acc acc agc atc tgt gcc ggc tac      1217
Phe Cys Pro Val Cys Ile Thr Phe Thr Thr Ser Ile Cys Ala Gly Tyr
         45                  50                  55 tgt cct agc atg gtgagctgac caaatgggta tggacatcac ttccgccta           1269
Cys Pro Ser Met
         60 cagtgctgct agcagtccta caggtggggg cgagggagta cagggagatg gcacggcagg     1329 gatcacagct actgtggggg caggaccagg tgggcattct gcctagaatg gctgcagggg     1389 gtggggaggg ggcgcagacc aggggaggga cactcagatg aggactttct ccaccctgca     1449 ctcag gtt cga gta ctg cca gct gcc ttg cct ccc gtg cct cag cca gtg    1499
      Val Arg Val Leu Pro Ala Ala Leu Pro Pro Val Pro Gln Pro Val
                65                  70                  75 tgc acc tac cgt gag ctg cgc ttc gcc tct gtc cgc ctc cct ggc tgc      1547
Cys Thr Tyr Arg Glu Leu Arg Phe Ala Ser Val Arg Leu Pro Gly Cys
         80                  85                  90 cca cct ggt gta gac ccc ata gtc tcc ttt cct gtg gcc ctc agc tgc      1595
Pro Pro Gly Val Asp Pro Ile Val Ser Phe Pro Val Ala Leu Ser Cys
         95                 100                 105 cgc tgt ggg ccc tgc cgt ctc agt agc tct gac tgt ggg ggt ccc agg      1643
Arg Cys Gly Pro Cys Arg Leu Ser Ser Ser Asp Cys Gly Gly Pro Arg
    110                 115                 120 act caa cca atg acc tgt gac ctt ccc cac ctc ccc ggc ctt ctc ctc      1691
Thr Gln Pro Met Thr Cys Asp Leu Pro His Leu Pro Gly Leu Leu Leu
125                 130                 135                 140 ttc tgatgccac ccactaactc ccattcttc tggagccagc aggtgttcta             1744
Phe accatccctc caataaagg ctttacaact gcactccgat gtcctttgtg taac            1798

<210> SEQ ID NO 2
<211> LENGTH: 141
<212> TYPE: PRT
<213> ORGANISM: Rattus norvegicus

<400> SEQUENCE: 2

Met Glu Arg Leu Gln Gly Leu Leu Leu Trp Leu Leu Leu Ser Pro Ser
1               5                   10                  15
```

```
Val Val Trp Ala Ser Arg Gly Pro Leu Arg Pro Leu Cys Arg Pro Val
         20                  25                  30

Asn Ala Thr Leu Ala Ala Glu Asn Glu Phe Cys Pro Val Cys Ile Thr
         35                  40                  45

Phe Thr Thr Ser Ile Cys Ala Gly Tyr Cys Pro Ser Met Val Arg Val
         50                  55                  60

Leu Pro Ala Ala Leu Pro Pro Val Pro Gln Pro Val Cys Thr Tyr Arg
 65                  70                  75                  80

Glu Leu Arg Phe Ala Ser Val Arg Leu Pro Gly Cys Pro Pro Gly Val
             85                  90                  95

Asp Pro Ile Val Ser Phe Pro Val Ala Leu Ser Cys Arg Cys Gly Pro
            100                 105                 110

Cys Arg Leu Ser Ser Ser Asp Cys Gly Gly Pro Arg Thr Gln Pro Met
            115                 120                 125

Thr Cys Asp Leu Pro His Leu Pro Gly Leu Leu Leu Phe
            130                 135                 140

<210> SEQ ID NO 3
<211> LENGTH: 1662
<212> TYPE: DNA
<213> ORGANISM: Homo sapiens
<220> FEATURE:
<221> NAME/KEY: CDS
<222> LOCATION: (550)..(564)
<220> FEATURE:
<221> NAME/KEY: CDS
<222> LOCATION: (917)..(1084)
<220> FEATURE:
<221> NAME/KEY: CDS
<222> LOCATION: (1319)..(1558)
<300> PUBLICATION INFORMATION:
<301> AUTHORS: Talmadge,K., Vamvakopoulos,N.C. and Fiddes,J.C.
<302> TITLE: Evolution of the genes for the beta subunits of human
       chorionic gonadotropin and luteinizing hormone
<303> JOURNAL: Nature
<304> VOLUME: 307
<305> ISSUE: 5946
<306> PAGES: 37-40
<307> DATE: 1984
<308> DATABASE ACCESSION NUMBER: NCBI/X00264
<309> DATABASE ENTRY DATE: 1997-07-31
<313> RELEVANT RESIDUES: (1)..(1662)

<400> SEQUENCE: 3
aagggagagg tggggctcgg gcttaatccc tccttggggg gcatctgggt caagtggctt    60
ccctggcagc acagtcacgg ggagaccctc tctcactggg cagaagctaa gtccgaagca   120
gcgcccctcc tgttaggttg gactgtggtg caggaaagcc tcaagtggag ggttgaggct   180
tcagtccagc acttttcctcg gtcatggcc tcctcctggc tcccaagacc ccacaattgg   240
cagaggcagg ccttcctaca ccctactccc tgtgcttcca gcctcgacta gtccctagca   300
ctcgacaact gagtctctga ggtcacttca ccgtggtctc tgcctcacct ctggcgctag   360 accccgtgagg ggagagggct ggggcactct gctgagccac tcctgcgcct ccctggccat   420
gtgcacctct cgcccccggg ggattagtgt ccaggttacc ccaggcatcc tatcacctcc   480
tggtggcctt gccgccccca caaccccgag gtataaagcc agatacacga ggcaggggat   540 gcaccaagg atg gag atg ctc cag gtaagactgc agggccctg gcaccttcc        594
           Met Glu Met Leu Gln
             1           5 acctccttcc aggccatcac tggcatgaga aggggcagac ccgtgtgagc tgtggaagga   654
ggcctctttc tggaggggcg tgaccccag taagcttcag gtggggcagt tcctgagggt    714
```

```
gggatctga aatgttgggg catctcaggt cctctgggct gtggggtggg ctctgaaagg      774
caggtgtccg ggtggtgggt cctgaatagg agatgccagg aagggtctct gggtctttgt      834
gggtggtgta ccacgcggga tgggaaggcc aggactcggg gctgcggtct cagacccggg      894
tgaagcagtg tccttgtccc ag ggg ctg ctg ctg ttg ctg ctg ctg agc atg      946
                         Gly Leu Leu Leu Leu Leu Leu Leu Ser Met
                                      10                       15 ggc ggg gca tgg gca tcc agg gag ccg ctt cgg cca tgg tgc cac ccc       994
Gly Gly Ala Trp Ala Ser Arg Glu Pro Leu Arg Pro Trp Cys His Pro
             20                  25                  30 atc aat gcc atc ctg gct gtg gag aag gag ggc tgc ccc gtg tgc atc      1042
Ile Asn Ala Ile Leu Ala Val Glu Lys Glu Gly Cys Pro Val Cys Ile
             35                  40                  45 acc gtc aac acc acc atc tgt gcc ggc tac tgc ccc acc atg              1084
Thr Val Asn Thr Thr Ile Cys Ala Gly Tyr Cys Pro Thr Met
             50                  55                  60 gtgagctgcc cggggccggg gcagatgctg ccacctcagg gccagaccca cagaggcagc     1144 ggggaggaa gggtggtctg cctctctggc ctgcggttgg ggaatggggt gtgggaaggc      1204
aggaacagag ggcttcctgg gctcctgagt ctgagacctg tggggtcagc ttgggagctc     1264
agctgaggcg ctggcctagg cacatgctca ttcccccact cacacggcct ccag atg      1321
                                                             Met cgc gtg ctg cag gcg gtc ctg ccg ccc ctg cct cag gtg gtg tgc acc      1369
Arg Val Leu Gln Ala Val Leu Pro Pro Leu Pro Gln Val Val Cys Thr
             65                  70                  75 tac cgt gat gtg cgc ttc gag tcc atc cgg ctc cct ggc tgc ccg cgt      1417
Tyr Arg Asp Val Arg Phe Glu Ser Ile Arg Leu Pro Gly Cys Pro Arg
             80                  85                  90 ggc gtg gac ccc gtg gtc tcc ttc cct gtg gct ctc agc tgt cgc tgt      1465
Gly Val Asp Pro Val Val Ser Phe Pro Val Ala Leu Ser Cys Arg Cys
95                  100                 105                 110 gga ccc tgc cgc cgc agc acc tct gac tgt ggg ggt ccc aaa gac cac      1513
Gly Pro Cys Arg Arg Ser Thr Ser Asp Cys Gly Gly Pro Lys Asp His
                 115                 120                 125 ccc ttg acc tgt gac cac ccc caa ctc tca ggc ctc ctc ttc ctc          1558
Pro Leu Thr Cys Asp His Pro Gln Leu Ser Gly Leu Leu Phe Leu
             130                 135                 140 taaagaccct ccccgcagcc ttccaagtcc atcccgactc ctggagccct gacaccccga     1618
tcctcccaca ataaaggctt ctcaatccgc actctggcag tatc                     1662

<210> SEQ ID NO 4
<211> LENGTH: 141
<212> TYPE: PRT
<213> ORGANISM: Homo sapiens

<400> SEQUENCE: 4

Met Glu Met Leu Gln Gly Leu Leu Leu Leu Leu Leu Ser Met Gly
1               5                   10                  15

Gly Ala Trp Ala Ser Arg Glu Pro Leu Arg Pro Trp Cys His Pro Ile
             20                  25                  30

Asn Ala Ile Leu Ala Val Glu Lys Glu Gly Cys Pro Val Cys Ile Thr
             35                  40                  45

Val Asn Thr Thr Ile Cys Ala Gly Tyr Cys Pro Thr Met Met Arg Val
             50                  55                  60

Leu Gln Ala Val Leu Pro Pro Leu Pro Gln Val Val Cys Thr Tyr Arg
65                  70                  75                  80
```

```
Asp Val Arg Phe Glu Ser Ile Arg Leu Pro Gly Cys Pro Arg Gly Val
            85                  90                  95

Asp Pro Val Val Ser Phe Pro Val Ala Leu Ser Cys Arg Cys Gly Pro
            100                 105                 110

Cys Arg Arg Ser Thr Ser Asp Cys Gly Gly Pro Lys Asp His Pro Leu
            115                 120                 125

Thr Cys Asp His Pro Gln Leu Ser Gly Leu Leu Phe Leu
            130                 135                 140
```

```
<210> SEQ ID NO 5
<211> LENGTH: 704
<212> TYPE: DNA
<213> ORGANISM: Homo sapiens
<220> FEATURE:
<221> NAME/KEY: CDS
<222> LOCATION: (102)..(452)
<300> PUBLICATION INFORMATION:
<308> DATABASE ACCESSION NUMBER: NCBINM_000735
<309> DATABASE ENTRY DATE: 2001-02-03
<313> RELEVANT RESIDUES: (1)..(704)

<400> SEQUENCE: 5
```

```
gcagttactg agaactcata agacgaagct aaaatccctc ttcggatcca cagtcaaccg      60
ccctgaacac atcctgcaaa aagcccagag aaaggagcgc c atg gat tac tac aga    116
                                              Met Asp Tyr Tyr Arg
                                               1               5 aaa tat gca gct atc ttt ctg gtc aca ttg tcg gtg ttt ctg cat gtt      164
Lys Tyr Ala Ala Ile Phe Leu Val Thr Leu Ser Val Phe Leu His Val
            10                  15                  20 ctc cat tcc gct cct gat gtg cag gat tgc cca gaa tgc acg cta cag      212
Leu His Ser Ala Pro Asp Val Gln Asp Cys Pro Glu Cys Thr Leu Gln
        25                  30                  35 gaa aac cca ttc ttc tcc cag ccg ggt gcc cca ata ctt cag tgc atg      260
Glu Asn Pro Phe Phe Ser Gln Pro Gly Ala Pro Ile Leu Gln Cys Met
    40                  45                  50 ggc tgc tgc ttc tct aga gca tat ccc act cca cta agg tcc aag aag      308
Gly Cys Cys Phe Ser Arg Ala Tyr Pro Thr Pro Leu Arg Ser Lys Lys
55                  60                  65 acg atg ttg gtc caa aag aac gtc acc tca gag tcc act tgc tgt gta      356
Thr Met Leu Val Gln Lys Asn Val Thr Ser Glu Ser Thr Cys Cys Val
70                  75                  80                  85 gct aaa tca tat aac agg gtc aca gta atg ggg ggt ttc aaa gtg gag      404
Ala Lys Ser Tyr Asn Arg Val Thr Val Met Gly Gly Phe Lys Val Glu
                90                  95                  100 aac cac acg gcg tgc cac tgc agt act tgt tat tat cac aaa tct taa      452
Asn His Thr Ala Cys His Cys Ser Thr Cys Tyr Tyr His Lys Ser
                105                 110                 115 atgttttacc aagtgctgtc ttgatgactg ctgattttct ggaatggaaa attaagttgt    512
ttagtgttta tggctttgtg agataaaact ctccttttcc ttaccatacc actttgacac    572
gcttcaagga tatactgcag ctttactgcc ttcctcctta tcctacagta caatcagcag    632
tctagttctt ttcatttgga atgaatacag cattaagctt gttccactgc aaataaagcc    692
ttttaaatca tc                                                         704
```

```
<210> SEQ ID NO 6
<211> LENGTH: 116
<212> TYPE: PRT
<213> ORGANISM: Homo sapiens

<400> SEQUENCE: 6
```

-continued

```
Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
        50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
            85                  90                  95

Gly Phe Lys Val Glu Asn His Thr Ala Cys His Cys Ser Thr Cys Tyr
            100                 105                 110

Tyr His Lys Ser
        115
```

METHODS OF REJUVENATING LEYDIG CELLS AND ENHANCING TESTOSTERONE PRODUCTION IN A MALE SUBJECT

CROSS REFERENCE TO RELATED APPLICATION

This application is based on and claims priority to U.S. Provisional Application Ser. No. 60/384,249, filed May 30, 2002, herein incorporated by reference in its entirety.

TECHNICAL FIELD

The presently claimed subject matter relates generally to in vivo methods of rejuvenating Leydig cells and enhancing the serum level of testosterone in a subject. More particularly, the presently claimed subject matter further relates to in vivo methods of rejuvenating Leydig cells and enhancing serum testosterone levels by coadministering TH and LH to a male subject. The presently claimed subject matter further relates to the treatment of a symptom of andropause in an aged male.

| Abbreviations | |
|---|---|
| 3-β-HSD | 3-β-hydroxysteroid dehydrogenase |
| ACTH | adrenocorticotropic hormone |
| cDNA | complementary DNA |
| CG | chorionic gonadotropin |
| CHO | Chinese hamster ovary |
| DNA | deoxyribonucleic acid |
| FSH | follicle stimulating hormone |
| hCG | human chorionic gonadotropin |
| HPTA | hypothalamic/pituitary testicular axis |
| LH | luteinizing hormone |
| M | month(s) |
| NCBI | National Center for Biotechnology Information |
| nt | nucleotide |
| P450scc | P450 side chain cleavage |
| PBS | phosphate buffered saline |
| pI | isoelectric point |
| RIA | radioimmunoassay |
| rLH | rat luteinizing hormone |
| QSAR | quantitative structure activity relationships |
| SEM | standard error of the mean |
| StAR | steroidogenic acute regulatory protein |
| TH | thyroid hormone |
| TSH | thyroid stimulating hormone |
| T3 | L-3,5,3'-triiodothyronine |
| T4 | L-3,5,3',5'-tetraiodothyronine; thyroxine |

Amino Acid Abbreviations and Functionally Equivalent Codons

| Amino Acid | 3-Letter | 1-Letter | Codons |
|---|---|---|---|
| Alanine | Ala | A | GCA GCC GCG GCU |
| Arginine | Arg | R | AGA AGG CGA CGC CGG CGU |
| Asparagine | Asn | N | AAC AAU |
| Aspartic Acid | Asp | D | GAC GAU |
| Cysteine | Cys | C | UGC UGU |
| Glutamic acid | Glu | E | GAA GAG |
| Glutamine | Gln | Q | CAA CAG |
| Glycine | Gly | G | GGA GGC GGG GGU |
| Histidine | His | H | CAC CAU |
| Isoleucine | Ile | I | AUA AUC AUU |
| Leucine | Leu | L | UUA UUG CUA CUC CUG CUU |
| Lysine | Lys | K | AAA AAG |
| Methionine | Met | M | AUG |
| Phenylalanine | Phe | F | UUC UUU |
| Proline | Pro | P | CCA CCC CCG CCU |
| Serine | Ser | S | ACG AGU UCA UCC UCG UCU |
| Threonine | Thr | T | ACA ACC ACG ACU |
| Tryptophan | Trp | W | UGG |
| Tyrosine | Tyr | Y | UAC UAU |
| Valine | Val | V | GUA GUC GUG GUU |

BACKGROUND

An effect of aging on male reproduction is the progressive decrease in sexual activity from adolescence into old age (Kinsey et al., (1948) *Sexual Behavior in the Human Male*, W.B. Saunders, Philadelphia, Pa., United States of America). This effect is often attributed to reduced circulating testosterone levels, which occur in all mammalian species studied to date, including humans (Hollander & Hollander, (1958) *J. Clin. Endocrinol.* 18:966-971; Kirschner & Coffman, (1968) *J. Clin. Invest.* 47:38-47; Vermeulen (1976) in: *Hypothalamus, Pituitary and Aging*, (Everitt & Burgess, eds.), Charles C. Thomas, Springfield, Ill., United States of America, pp. 458-463) and rats (Harman et al., (1978) *Endocrinol.* 102:540-544; Bethea & Walker, (1979) *J. Gerontology* 34:21-27; Chen et al., (1994) *J. Androl.* 15:551-557; and Mendis-Handagama & Gelber, (1995) *Tissue Cell* 27:689-699). Testosterone is necessary in the male reproductive system for many functions, including the regulation of spermatogenesis in the testis, maintenance of the accessory sex organs, and erectile function (Morales et al., (1996) *Int. J. Impotence Res.* 8:95-97 and Norman & Litwack, (1997) in: *Hormones* (Norman & Litwack, eds.), Academic Press, San Diego, Calif., United States of America, pp. 169-191).

Testosterone is also required by other organ systems of the mammalian male for their proper functioning. These include, but are not limited to, the brain (for libido and mood), skin (for hair growth and sebaceous gland activity), muscle (to increase muscle strength volume), liver (to synthesize serum proteins), synovial tissue (to modulate immune responses), bone (to maintain strength and volume), bone marrow (to stimulate stem cells), and kidney (to stimulate erythropoietin) (Morales et al., (1996) *Int. J. Impotence Res.* 8:95-97; Norman & Litwack, (1997) in: *Hormones* (Norman & Litwack, eds.), Academic Press, San Diego, Calif., United States of America, pp. 169-191; Anderson et al., (1996) *Bone* 18:171-177; and Gooren, (1996) *Br. J. Urol.* 78:763-768). Therefore, sustaining the normal levels of circulating testosterone clearly is important for the well being of the male.

Testosterone is primarily produced by the Leydig cells in the testis. Many studies regarding the effects of aging on Leydig cell structure and function have revealed that Leydig cells undergo atrophic changes in size with aging, thus enabling them go into a malfunctioning status (Chen et al., (1994) *J. Androl.* 15:551-557 and Mendis-Handagama & Gelber, (1995) *Tissue Cell* 27:689-699) and organelle content (Ichihara et al., (1993) *Cell Tissue Res.* 271:241-255 and Mori et al., (1982) *J. Clin. Endocrinol. Metab.* 55:634-641).

A journal article by Valenti et al. attempts to address Leydig cell function (Valenti et al., (1997) *International J.*

*Andrology* 20(5):279-86). Valenti et al. made adult rats (90 days old) hypothyroidic and examined Leydig cells extracted from the hypothyroidic rats in the presence or absence of several stimuli, notably luteinizing hormone (LH). Thus, Valenti et al. performed in vitro experiments.

A journal article by Maran et al. disclosed a study of the effect of L-3,5,3'-triiodothyronine (T3) on LH-mediated synthesis and secretion of testosterone by Leydig cells in vitro (Maran et al., (2000) *Endocr. J.* 47:417-28). Maran et al. found that T3 increased testosterone secretion of Leydig cells in a dose dependent fashion up to 50 ng, above which the stimulatory effect was attenuated. Additionally, Maran et al. found that while the minimum effective dose of T3 for testosterone production (25 ng) potentiated the equivalent stimulatory effect of the minimum effective dose of LH (100 ng), 50 ng of T3 attenuated the effect of either LH or T3 dose. Again, the studies of Maran et al. were in vitro. Additionally, the Leydig cells were isolated from young rats: i.e., 60 days old. 60-day-old rats are described as being just at puberal maturation.

Currently, androgen deficiencies in aging humans are treated with androgen therapy (Anderson et al., (1996) *Bone* 18:171-177 and Gooren, (1996) *Br. J. Urol.* 78:763-768). The risks of administering androgens to aging men mainly concern the cardiovascular system and the prostate (Gooren, (1996) *Br. J. Urol.* 78:763-768). Cardiovascular effects of androgens are ascribed to the atherogenic effects of androgens on blood-lipid profiles (Gooren, (1996) *Br. J. Urol.* 78:763-768). Apart from these effects, androgens can have other possible deleterious metabolic effects on the cardiovascular system. They induce insulin resistance (Polderman et al., (1994) *J. Clin. Endocrinol. Metab.* 79:275-281) and increased plasma levels of endothelin, a substance with vasoconstrictor properties produced by the vascular wall (Polderman et al., (1993) *Ann. Intern. Med.* 118:429-432). Regarding the effects of androgens on the prostate, benign prostatic hyperplasia and prostate cancer are the main concerns (Polderman et al., (1993) *Ann. Intern. Med.* 118:429-432).

In summary, there is a current need in the art for new and improved approaches for enhancing testosterone levels and/or for restoring Leydig cell function in a subject in need thereof. The presently claimed subject matter addresses these and other problems.

SUMMARY

In one aspect of the presently claimed subject matter, a method for rejuvenating Leydig cells in a male subject having Leydig cells is disclosed. In one embodiment, the method comprises: (a) providing a male subject having Leydig cells; and (b) coadministering luteinizing hormone (LH) and thyroid hormone (TH) to the subject, whereby rejuvenation of Leydig cells in a male subject having Leydig cells is accomplished. In one embodiment, the male subject is a mammal, and in another embodiment the male subject is a human male. The subject is in one embodiment aged and/or has atrophied Leydig cells. The TH can comprise L-3,5,3',5'-tetraiodothyronine (T4; also called tetraiodothyronine or thyroxine) or L-3,5,3'-triiodothyronine (T3; also called triiodothyronine). Additionally, the TH and LH can comprise a therapeutic composition, which can also comprise additional components. The TH and LH can be coadministered contemporaneously, in one embodiment by an implanted pump and in another embodiment by an osmotic pump. Transdermal drug delivery systems, such as skin patches, can also be employed.

In another aspect of the presently claimed subject matter, a method of enhancing testosterone production in a male subject having Leydig cells is disclosed. In one embodiment, the method comprises: (a) providing a male subject having Leydig cells and a serum testosterone level less than desired level; and (b) coadministering luteinizing hormone (LH) and thyroid hormone (TH) to the subject, whereby testosterone production in a male subject having Leydig cells is enhanced. In one embodiment, the male subject is a mammal, and in another embodiment, the male subject is a human male. The subject is in one embodiment aged and/or has atrophied Leydig cells. The TH can comprise T4 or T3. Additionally, the TH and LH can comprise a therapeutic composition, which can also comprise additional components. The TH and LH can be coadministered contemporaneously, in one embodiment by an implanted pump and in another embodiment by an osmotic pump. Transdermal drug delivery systems, such as skin patches, can also be employed.

In yet another embodiment of the presently claimed subject matter, a method of treating a symptom of andropause in an aged male subject having Leydig cells is disclosed. In one embodiment, the method comprises: (a) providing an aged male subject having Leydig cells and undergoing andropause; and (b) coadministering luteinizing hormone (LH) and thyroid hormone (TH) to the subject, whereby a symptom of andropause is treated in an aged male subject having Leydig cells. In one embodiment, the male subject is a mammal, and in another embodiment, the male subject is a human male. The subject is in one embodiment aged and has atrophied Leydig cells. The TH can comprise T4 or T3. Additionally, the TH and LH can comprise a therapeutic composition, which can also comprise additional components. The TH and LH can be coadministered contemporaneously, in one embodiment by an implanted pump and in another embodiment by an osmotic pump. Transdermal drug delivery systems, such as skin patches, can also be employed.

Accordingly, it is an object of the presently claimed subject matter to rejuvenate Leydig cells in a male subject. This object is achieved in whole or in part by the presently claimed subject matter.

An object of the presently claimed subject matter having been stated hereinabove, other objects will be evident as the description proceeds, when taken in combination with the accompanying Drawings and Examples as best described hereinbelow.

BRIEF DESCRIPTION OF THE SEQUENCE LISTING

Figure 1A:
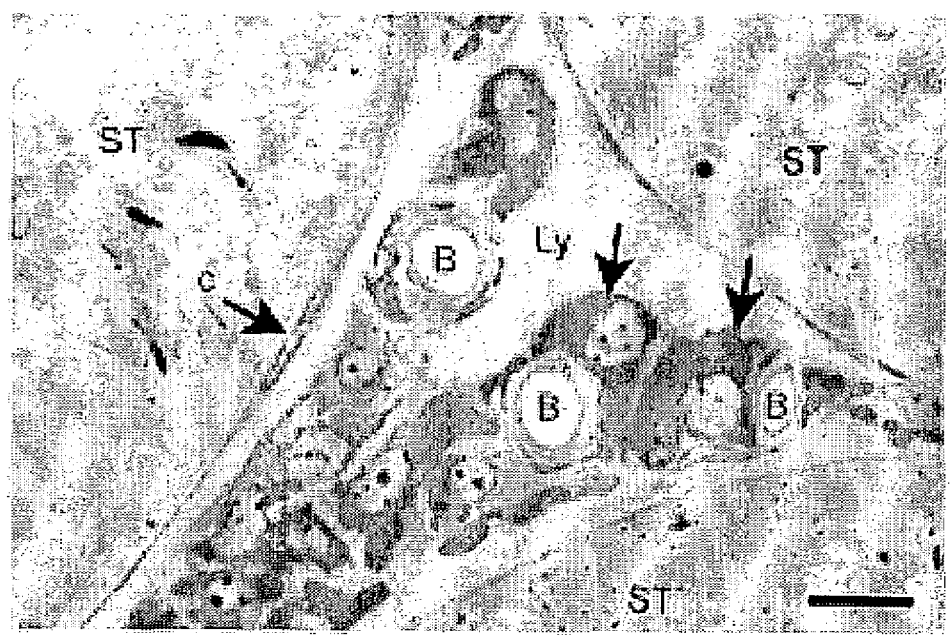
FIG. 1A is a light micrograph of testis interstitium of brown Norway rats aged 3 months. Arrows depict Leydig cells. c indicates connective tissue cells; Ly indicates lymphatic space; M indicates macrophages; ST indicates seminiferous tubules. Bar=7.7 μm, same magnification for all micrographs.

SEQ ID NO: 1 is a DNA sequence encoding a *Rattus norvegicus* LH β subunit polypeptide (National Center for Biotechnology Information (NCBI) Accession No. J00749).

SEQ ID NO: 2 is an amino acid sequence of a *Rattus norvegicus* LH β subunit polypeptide (NCBI Accession No. NP_036990).

SEQ ID NO: 3 is a DNA sequence encoding a human LH β subunit polypeptide (NCBI Accession No. X00264).

SEQ ID NO: 4 is an amino acid sequence of a human LH β subunit polypeptide (NCBI Accession No. P01229).

SEQ ID NO: 5 is a DNA sequence encoding a human glycoprotein hormone α subunit (NCBI Accession No. NM_00735).

SEQ ID NO: 6 is an amino acid sequence of a human glycoprotein hormone α subunit (NCBI Accession No. NP_00726).

DETAILED DESCRIPTION

Until disclosure of the presently claimed subject matter as presented herein, the ability to rejuvenate Leydig cells in a male subject having Leydig cells and/or to enhance testosterone levels in vivo in such a subject had not been realized. And until disclosure of the presently claimed subject matter presented herein, the finding that coadministering TH and LH to a male subject in need thereof results in elevation of serum testosterone levels had not been reported. These and other observations form aspects of the presently claimed subject matter and are discussed further herein below.

In summary, the presently claimed subject matter provides for the coadministration of LH and TH to a subject to enhance testosterone levels and/or to restore Leydig cell function. The administration of LH alone or TH alone is not sufficient to restore atrophied Leydig cells to a desired level of function. Further, administration of each agent alone is not sufficient to treat andropause or to treat an aged subject. Thus, what is needed is a method of enhancing serum testosterone levels to a desired level. Additionally, a method of rejuvenating Leydig cells is also needed. The presently claimed subject matter addresses these and other objects.

I. DEFINITIONS

Following long-standing patent law convention, the terms "a" and "an" mean "one or more" when used in this application, including the claims.

As used herein, the term "about", when referring to a value or to an amount of mass, weight, time, volume, concentration, or percentage, is meant to encompass variations of in one embodiment ±20%, in another embodiment ±10%, in another embodiment ±5%, in another embodiment ±1%, and in still another embodiment ±0.1% from the specified amount, as such variations are appropriate to perform the disclosed method.

As used herein, the term "aged" generally describes a condition or set of conditions that are typically observed in a subject of advancing chronological age, in one embodiment at least about 30 years of age in a human subject, in another embodiment from between 30 and 70 years of age in a human subject (including any age within this range, such as, for example, 35, 40, 45, 50, 55, 60, and 65 years of age), and in still another embodiment older than 70 years of age in a human subject (for example, 75, 80, 85 or 90 years of age). The term "aged" also describes a condition or conditions that appear in a young subject (e.g., less than 30 years of age in a human subject) that are typically observed in subjects that are older (e.g., 30-70 years of age in a human subject).

One condition typically observed in a male subject of advanced age is a reduced serum testosterone level. For example, in a human subject, a representative reduced serum testosterone level is less than about 250 ng/100 ml. Thus, generally, the term "aged" refers to a diminished capacity of the testis and Leydig cells to secrete testosterone at normal basal levels. Representative normal basal levels can range, for example, from about 250 ng/100 ml to about 1250 ng/100 ml. A human subject having a serum testosterone level of less than about 250 ng/100 ml can thus be defined as "aged", regardless of chronological age.

In the context of a Leydig cell, the term "aged Leydig cell" refers to a Leydig cell that is not secreting, and/or is not capable of secreting, testosterone in an amount associated with normal Leydig cell activity. A representative serum level of testosterone in a male is at least about 250 ng/100 ml blood.

As used herein, the term "biological activity" refers to any observable biological effect including, but not limited to, an effect flowing from interaction between LH and TH and a Leydig cell. Representative, but non-limiting, examples of biological activity in the context of the presently claimed subject matter include rejuvenation of Leydig cells and an enhancement of serum testosterone levels.

As used herein, the term "contemporaneous", and grammatical derivations thereof, takes its common meaning and refers to two or more events that occur at or about the same time. In one aspect of the presently claimed subject matter, LH and TH can be administered to a subject contemporaneously. In this aspect, LH and TH are administered to the subject at the same time. In another aspect of the presently claimed subject matter, LH and TH can be coexistent in a single formulation, which is itself administered to a subject.

As used herein, the terms "LH" and "luteinzing hormone" are used interchangeably and refer to a polypeptide comprising all of one of the amino acid sequence of SEQ ID NOs: 2, 4, and 6, or a fragment thereof, wherein the polypeptide is biologically active. The terms also encompass LH mutant and chimeric polypeptides as well as structural and biological equivalents of LH.

As used herein, the terms "LH" and "luteinzing hormone" also refer to nucleic acids encoding a luteinizing hormone polypeptide that can associate with a Leydig cell, such as, for example, the nucleic acid sequences set forth in SEQ ID NOs: 1, 3, and 5. The terms include invertebrate homologs; however, in one embodiment, LH nucleic acids and polypeptides are isolated from vertebrate sources. "LH" further includes vertebrate homologs of LH family members, including, but not limited to, mammalian and avian homologs. Representative mammalian homologs of LH family members include, but are not limited to, rat, mouse and human homologs. The terms encompass nucleic acids that can hybridize to the nucleic acid sequence SEQ ID NOs: 1, 3, and 5 under stringent conditions.

As used herein, the terms "patient" and "subject" are used interchangeably and refer to any organism for which is it desired to effect a change from the organism's present state. A subject can be, for example, an aged male with atrophied Leydig cells. Alternatively, a subject can be a male that has a lower-than-desired serum testosterone level. Broadly, then, a "patient" or "subject" is an organism on which the presently claimed subject matter is practiced for any purpose. As used herein, the terms "patient" and "subject" need not refer exclusively to human beings, but rather the terms encompass all organisms for which it is desired to rejuvenate atrophied Leydig cells and/or for which it is desired to raise the level of serum testosterone and/or for which is it is desired to treat a symptom of andropause. These are only a few specific applications of the presently claimed subject matter, and the terms "patient" and "subject" can be employed to generally refer to the organism on which manipulation is performed. The terms refer in one embodiment to all mammals, and in another embodiment refer to humans, rats, and mice. The terms encompass all mammals and birds. In one embodiment, the animal can be selected from the group consisting of rodent, swine, bird, ruminant, and primate. In another embodiment, the animal can be selected from the group consisting of a mouse, a rat, a pig, a guinea pig, poultry, an emu, an ostrich, a goat, a cow, a sheep, and a rabbit. And in still another embodiment, the animal can be a primate, such as an ape, a monkey, a lemur, a tarsier, a marmoset, or a human.

Thus, provided is the treatment of mammals such as humans, as well as those mammals of importance due to being endangered (such as Siberian tigers), of economical importance (animals raised on farms for consumption by humans), and/or of social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses (such as thoroughbreds). Also provided is the treatment of birds, including the treatment of those kinds of birds that are endangered or kept in zoos, as well as fowl, and more particularly domesticated fowl, e.g., poultry, such as turkeys, chickens, ducks, geese, guinea fowl, and the like, as they are also of economical importance to humans. Thus, provided is the treatment of livestock, including, but not limited to, domesticated swine (pigs and hogs), ruminants, horses, poultry, and the like.

As used herein, the term "rejuvenating Leydig cells", and grammatical derivations thereof, refers to restoring decreased Leydig cell function to a desired level. A representative desired level can be a level associated with basal activity levels in a subject of the same species having healthy Leydig cells. For example, a Leydig cell function can be secretion of testosterone. A representative desired level of serum testosterone can be at least about 250 ng/100 ml and can also range between about 250 ng/100 ml and about 1250 ng/100 ml blood serum. The term generally encompasses effecting a change in any function so that the function is generally equivalent to that function and normally carried out by a Leydig cell disposed in a healthy organism. The term specifically includes restoring testosterone production to a desired level, such as at least about 250 ng/100 ml about 350 ng/100 ml, about 450 ng/100 ml, about 550 ng/100 ml, about 650 ng/100 ml, about 750 ng/100 ml, about 850 ng/100 ml, about 950 ng/100 ml, about 1050/100 ml, about 1150 ng/100 ml, about 1250 ng/100 ml and ranges therein. When a Leydig cell is rejuvenated, it is not necessary that the cell undergo a morphological change, although an increase in cell volume can occur. The extent of rejuvenation can be characterized in terms of Leydig cell function, e.g., the production of testosterone and/or other hormones, production of proteins and/or peptides, the ability to bind small molecules, hormones, etc., as well as other Leydig cell functions. Approaches for evaluating Leydig cell function are disclosed in the Examples presented below.

As used herein, the terms "thyroid hormone" and "TH" are used interchangeably herein and refer to any hormone produced and/or processed in a thyroid gland. The term specifically encompasses the compounds T3 and T4, but can also include other compounds produced by and/or processed in a thyroid gland. The terms also include synthetic analogs and functional equivalents of T3, T4, and other compounds produced by and/or processed in a thyroid gland.

As used herein, the terms "triiodothyronine" and "T3" are used interchangeably and refer to the thyroid hormone represented by the following chemical structure:

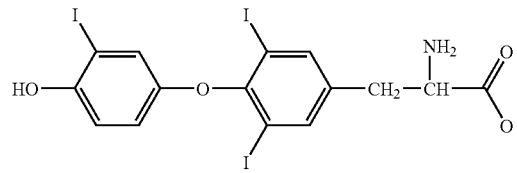

The terms "triiodothyronine" and "T3" also include analogs, derivatives, and equivalents of T3, including, but not limited to analogs, derivatives, and functional equivalents that are designed, developed, or synthesized using the chemical structure of T3 as a starting point, or that are designed, developed, or synthesized via another approach.

As used herein, the terms "tetraiodothyronine", "thyroxine", and "T4" are used interchangeably and refer to the thyroid hormone represented by the following chemical structure:

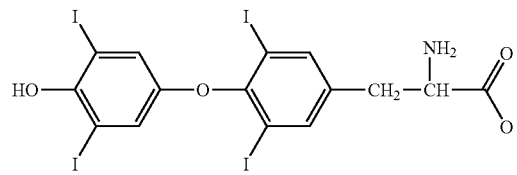

The terms "tetraiodothyronine", "thyroxine", and "T4" also include analogs, derivatives, and equivalents of T4 that are designed, developed, or synthesized using the chemical structure of T4 as a starting point, or that are designed, developed, or synthesized via another approach.

As used herein, the term "therapeutic composition" refers to a chemical entity intended to effectuate a change in an organism. It is not necessary that a therapeutic composition be known to effectuate a change in an organism; chemical entities that are suspected, predicted, or designed to effectuate a change in an organism are therefore encompassed by the term "therapeutic composition". The effectuated change can be of any kind, observable or unobservable, and can include, for example, a change in the biological activity of a cell, such as a Leydig cell.

Therapeutic compositions can comprise small molecules, proteins and/or peptides, oligonucleotides of any length, "xenobiotics", such as drugs, natural products and extracts, as well as "endobiotics." Therapeutic compositions can also comprise, but are not restricted to hormones (e.g., opioid peptides, steroids, etc.), hormone receptors, peptides, enzymes, enzyme substrates, co-factors, lectins, sugars, oligonucleotides or nucleic acids, oligosaccharides, proteins, small molecules, and monoclonal antibodies.

A therapeutic composition can also comprise other substances such as buffers, water, minerals, carrier proteins, and other excipients known to one skilled in the art. In one embodiment, a therapeutic composition is adapted for administration to a subject, in one embodiment a mammalian subject and in another embodiment a human subject.

In one embodiment, the term "therapeutic composition" encompasses a composition comprising LH and/or TH (either as T3 or T4). A therapeutic composition can also encompass a chemical entity that activates and/or enhances expression of LH.

II. GENERAL CONSIDERATIONS

The testis of male animals, including humans, is divided into two compartments. One compartment, which is responsible for the production of sperm, contains a tightly packed series of tubular coils known as the seminiferous tubules. The seminiferous tubules make up the majority of the testes structure. Hormone-producing cells located within the seminiferous tubules that assist in the transformation of germ cells to sperm cells are known as Sertoli cells. The other compartment of the testis contains Leydig cells. Leydig cells are responsible for the production of androgens or male sex hormones. The Leydig cells are interspersed between the various coils of the seminiferous tubules.

The Leydig cells, located in the interstitial compartment and comprising approximately 2-3% of the total testicular cell number in most species, are the only cells in the testis that contain two key steroidogenic enzyme pathways, namely, cytochrome P450 side chain cleavage (P450scc) and 3-β-hydroxysteroid dehydrogenase (3-β-HSD). Thus, Leydig cells are the only testicular cells capable of the first two steps in steroidogenesis, namely (i) the conversion of cholesterol, the substrate for all steroid hormones, to pregnenolone; and (ii) the conversion of pregnenolone to progesterone. Therefore, the interstitial compartment in general, and the Leydig cells in particular, synthesize virtually all of the steroids produced in the testis, with testosterone being the major steroid biosynthesized in the adult male.

A major stimulus for the biosynthesis of testosterone in the Leydig cell is the gonadotrophic hormone, luteinizing hormone (LH). LH is secreted from specific cells located in the anterior pituitary and it interacts with specific receptors on the surface of the Leydig cell and initiates the signal for testosterone production. Cellular events occur rapidly in response to the trophic hormone stimulation of Leydig cells, and result in the synthesis and secretion of testosterone. These rapid or acute effects of hormone stimulation occur within minutes and can be distinguished temporally from the slower chronic effects that occur on the order of many hours and that involve mechanisms to increase gene transcription and translation of the steroid hydroxylase cytochrome P450 enzymes involved in the biosynthesis of these steroids.

The thyroid hormones triiodothyronine (T3) and tetraiodothyronine (T4; also called thyroxine) are major metabolic regulators in mammals. T4 and T3 are produced by the follicular cells of the thyroid gland and are regulated by thyroid stimulating hormone (TSH) made by the thyrotrophs of the anterior pituitary gland. T4 is less active than T3, and can be converted to T3 in peripheral tissues. Generally, administration of T4 or T3 to a subject increases metabolism, erythropoiesis, bone turnover, and the rate of muscle relaxation. T4 and T3 are synthesized from tyrosine and iodine bound to thyroglobulin, a protein. Two iodinated tyrosines are condensed to form a molecule of T4 or T3. Thyroglobulin, which is stored extracellularly in the follicular lumen of the thyroid gland, acts as a storage molecule for the iodinated tyrosine residues. Iodinated tyrosine residues are released from thyroglobulin by intracellular proteolysis in thyroid cells.

Research into "male menopause" or "andropause" has indicated that there is a drastic drop of serum levels of free testosterone of about 1.5% per year. While the total testosterone of a male does not drop drastically, the free testosterone, which is the biologically active fraction of the systemic testosterone concentration, does drop precipitously with aging. In fact, in human males, a significant drop of free testosterone can occur as early as the early 40s. The observed decrease in testosterone production is accompanied by an atrophying of Leydig cells in mammalian males. Thus, as a mammalian male ages, an increasingly large number of Leydig cells atrophy, with a concomitant decrease in testosterone production. The term "aged male subject" is meant to encompass any male subject suffering from this condition.

Testosterone is the principal male hormone and is required for the development and maintenance of secondary sexual characteristics, libido, and spermatogenesis. Testosterone also has anabolic properties, promoting muscle growth and maintenance. Lower than normal testosterone levels in males has been associated with low energy, frailty, depression, decreased libido, weakness, lethargy, loss of lean body and bone mass, impotence, and infertility. Indeed, approximately 5 percent of American couples are infertile due to male infertility alone (approximately 2.5 million men), and 75 percent of these males have pathologies associated with low testosterone output by the testes (approximately 1.9 million men). Rejuvenation of Leydig cells, and consequently elevation of serum testosterone levels, can be efficacious in increasing the fertility of many of these men.

In one aspect, the presently claimed subject matter comprises a method of rejuvenating Leydig cells and, consequently, stimulating testosterone production in a male subject. Often, the condition of low testosterone serum levels accompanies advancing age and associated conditions (e.g., andropause). A common treatment for this condition is the direct injection of testosterone into the subject. However, this treatment is not without drawbacks. For example, therapy involving the direct injection of testosterone is contraindicated for individuals afflicted with a cardiovascular condition and/or prostate disease. As males age, they are prone to the development of these conditions, making this type of therapy undesirable.

Generally, the presently claimed subject matter comprises a method of rejuvenating Leydig cells and boosting testosterone production by those cells, resulting in an increase in the serum level of testosterone. In one embodiment, the method comprises coadministering luteinizing hormone (LH) and thyroid hormone (TH) to a male subject having Leydig cells. In vivo data generated in a rat model system and disclosed herein indicates a 100% reversal of atrophied and malfunctioning Leydig cells in 19-month-old rats, returning them to the condition of a 3-month-old rat. Testosterone production was concurrently elevated. A form of this therapy can be employed to combat andropause in human males by rejuvenating Leydig cells and concomitantly boosting testosterone production. This treatment rationale can also be employed to enhance the fertility of a mammalian male that is suffering from infertility due to decreased serum levels of testosterone.

III. LH AND TH FORMULATIONS

In one aspect of the presently claimed subject matter, LH and TH are coadministered to a subject. LH is a gonadotropin that comprises two subunits, the α subunit and the β subunit, and is presented in SEQ ID NOs: 1-6.

The term "TH" includes both T3, which has the chemical structure

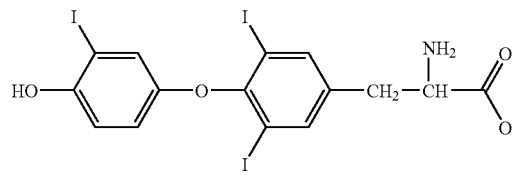

and T4, which has the chemical structure

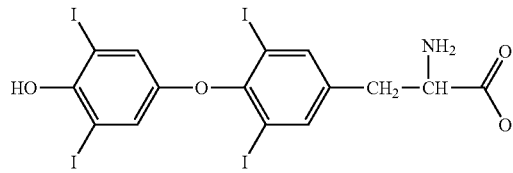

In the presently claimed subject matter, these compounds can be administered to a subject, and therefore in one embodiment the LH and TH are maintained as pharmaceutically acceptable formulations. As used herein, the compounds of the presently claimed subject matter (e.g., LH and TH) include pharmaceutically acceptable derivatives thereof. As used herein, the term "pharmaceutically acceptable derivative" refers to any pharmaceutically acceptable salt, ester, or salt of such ester, of a compound of the presently claimed subject matter or any other compound which, upon administration to a recipient, is capable of providing (directly or indirectly) a compound of the presently claimed subject matter to the organism with no adverse effects associated with the form in which the compound is presented to the organism.

Pharmaceutically acceptable salts of the compounds of the presently claimed subject matter include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicylic, succinic, toluene-p-sulfonic, tartaric, acetic, citric, methanesulfonic, formic, benzoic, malonic, naphthalene-2-sulfonic, and benzenesulfonic acids. Other acids, such as oxalic, while not in themselves pharmaceutically acceptable, can be employed in the preparation of salts useful as intermediates in obtaining the compounds of the presently claimed subject matter and their pharmaceutically acceptable acid addition salts.

LH and TH can form components of a solution that is introduced to an organism. Such a solution can comprise a buffer that makes the solution isotonic and/or maintains the solution at a desired pH. In one embodiment, a buffer is phosphate buffered saline (PBS). A solution can also comprise a pharmaceutically acceptable excipient, a carrier protein, or other compound known or suspected to enhance or assist in the delivery of an LH or TH molecule to desired tissue or site (e.g., a receptor on a Leydig cell).

In other embodiments of the presently claimed subject matter, it might be desirable to include additional components adapted to enhance the rejuvenation of Leydig cells or to enhance serum levels of testosterone. Such components can be added to a solution comprising LH, TH, or both. A non-limiting list of suitable additional components includes proteins and/or peptides, hormones, and small molecules. Commercially available therapeutics can also be employed as additional components. A therapeutic composition can also encompass a chemical entity that activates and/or enhances expression of LH as well as a gene therapy vector encoding LH. Thus, the phrases "administering LH" and "coadministering LH and TH" encompass administering a chemical entity that activates and/or enhances expression of endogenous LH as well as administering a gene therapy vector encoding LH. In one embodiment, the gene therapy vector comprises an LH-encoding nucleic acid as disclosed herein.

LH and TH can be purchased commercially (these compounds are available from various commercial suppliers, for example, Sigma Chemicals, St. Louis, Mo., United States of America). Alternatively, TH can be synthesized by employing synthetic pathways known to those of ordinary skill in the art. LH and TH can also be isolated from cell and tissue cultures by employing isolation techniques known to those of ordinary skill in the art.

III.A. Compounds Sterically Similar to LH

A further aspect of the presently claimed subject matter is that sterically similar compounds can be formulated to mimic the key portions of an LH polypeptide structure. Such compounds are structural functional equivalents. The generation of a structural functional equivalent can be achieved by the techniques of modeling and chemical design known to those of skill in the art and described herein. Modeling and chemical design of LH structural equivalents can be based on the structural coordinates of a crystalline LH polypeptide (e.g., the β subunit of human LH, National Center for Biotechnology Information (NCBI) Accession No. P01229), or equivalents can be designed and built based on a model constructed using a primary sequence of an LH polypeptide. It will be understood that all such sterically similar constructs fall within the scope of the presently claimed subject matter.

The terms "gene expression" and "expression" are used interchangeably and generally refer to the cellular processes by which a biologically active polypeptide is produced from a DNA sequence. Generally, gene expression comprises the processes of transcription and translation, along with those modifications that normally occur in the cell to modify the newly translated protein to an active form and to direct it to its proper subcellular or extracellular location.

The term "gene" refers broadly to any segment of DNA associated with a biological function. A gene encompasses sequences including, but not limited to a coding sequence, a promoter region, a transcriptional regulatory sequence, a non-expressed DNA segment that is a specific recognition sequence for regulatory proteins, a non-expressed DNA segment that contributes to gene expression, a DNA segment designed to have desired parameters, and combinations thereof. A gene can be obtained by a variety of methods, including isolation or cloning from a biological sample, synthesis based on known or predicted sequence information, and recombinant derivation of an existing sequence. As will be understood by those in the art, this functional term includes both genomic sequences and cDNA sequences. Representative embodiments of genomic and cDNA sequences are disclosed herein.

As used herein, the term "mutation" carries its traditional connotation and means a change, inherited, naturally occurring, or introduced, in a nucleic acid or polypeptide sequence, and is used in its sense as generally known to those of skill in the art.

As used herein, the term "polypeptide" means any polymer comprising any of the 20 protein amino acids, regardless of its size. Although "protein" is often used in reference to relatively large polypeptides, and "peptide" is often used in reference to small polypeptides; usage of these terms in the art overlaps and varies. The term "polypeptide" as used herein refers to peptides, polypeptides, and proteins, unless otherwise noted. As used herein, the terms "protein", "polypeptide", and "peptide" are used interchangeably herein when referring to a gene product.

As used herein, the terms "chimeric protein" or "fusion protein" are used interchangeably and refer to a fusion of a first amino acid sequence encoding an LH polypeptide with a second amino acid sequence defining a polypeptide domain foreign to, and not homologous with, any domain of one of an LH polypeptide. A chimeric protein can represent a foreign domain that is found in an organism that also expresses the first protein, or it can be an "interspecies" or "intergenic" fusion of protein structures expressed by different kinds of organisms. In general, a fusion protein can be represented by the general formula X—LH—Y, wherein LH represents a portion of the protein which is derived from an LH polypeptide, and X and Y are independently absent or represent amino acid sequences which are not related to an LH sequence in an organism, which includes naturally occurring mutants. The term "chimeric gene" refers to a nucleic acid construct that encodes a "chimeric protein" or "fusion protein" as defined herein.

As used herein, the term "isolated" refers to oligonucleotides substantially free of other nucleic acids, proteins, lipids, carbohydrates, or other materials with which they can be associated, such association being either in cellular material or in a synthesis medium. The term can also be applied to polypeptides, in which case the polypeptide will be substantially free of nucleic acids, carbohydrates, lipids and other undesired polypeptides. The term can also be applied to cells, in which usage the term refers to one or more cells removed from an organism in which the cells normally reside, in which the cells have been implanted, or in which the cells have been induced to grow.

As used herein, the term "substantially pure" refers to a compound (e.g., a polynucleotide, polypeptide, hormone, etc.) that is substantially free of the sequences and molecules with which it is associated in its natural state, and those molecules used in an isolation procedure. The term "substantially free" means that the sample is in one embodiment at least 50%, in another embodiment at least 70%, in another embodiment at least 80% and in still another embodiment at least 90% free of the materials and compounds with which is it associated in nature or which are employed in an isolation process.

As used herein, the term "DNA sequence encoding an LH polypeptide" can refer to one or more coding sequences within a particular individual. Moreover, certain differences in nucleotide sequences can exist between individual organisms, which are called alleles. It is possible that such allelic differences might or might not result in differences in amino acid sequence of the encoded polypeptide yet still encode a protein with substantially the same biological activity. As is well known, genes for a particular polypeptide can exist in single or multiple copies within the genome of an individual. Such duplicate genes can be identical or can have certain modifications, including nucleotide substitutions, additions, or deletions, all of which still encode polypeptides having substantially the same activity. A representative "DNA sequence encoding an LH polypeptide" is set forth as SEQ ID NOs: 1, 3, or 5.

As used herein, the terms "LH gene product", "LH protein", "LH polypeptide", and "LH peptide" are used interchangeably and refer to peptides having amino acid sequences which are substantially identical to native amino acid sequences from an organism of interest (e.g., SEQ ID NOs: 2, 4, and 6) and which are biologically active in that they comprise all or a part of the amino acid sequence of an LH polypeptide, or cross-react with antibodies raised against an LH polypeptide, or retain all or some of the biological activity (e.g., the ability to associate with a Leydig cell) of the native amino acid sequence or protein.

As used herein, the terms "LH gene product", "LH protein", "LH polypeptide", and "LH peptide" also include analogs of an LH polypeptide. By "analog" it is intended that a DNA or peptide sequence can contain alterations relative to the sequences disclosed herein yet retain all or some of the biological activity of those sequences. Analogs can be derived from genomic nucleotide sequences as are disclosed herein or from other organisms, or can be created synthetically. Those skilled in the art will appreciate that other analogs, as yet undisclosed or undiscovered, can be used to design and/or construct LH analogs. There is no need for a "LH gene product", "LH protein", "LH polypeptide", or "LH peptide" to comprise all or substantially all of the amino acid sequence of an LH polypeptide gene product. Shorter or longer sequences are anticipated to be of use in the presently claimed subject matter; shorter sequences are herein referred to as "segments". Thus, the terms "LH gene product", "LH protein", "LH polypeptide", and "LH peptide" also include fusion, chimeric, or recombinant LH polypeptides and proteins comprising sequences of the presently claimed subject matter. Methods of preparing such proteins are disclosed herein and are known to those of ordinary skill in the art.

As used herein, the terms "LH gene" and "recombinant LH gene" refer to a nucleic acid molecule comprising an open reading frame encoding an LH polypeptide of the presently claimed subject matter, including both exon and (optionally) intron sequences.

As used herein, the term "transcription" refers to a cellular process involving the interaction of an RNA polymerase with a gene that directs the expression as RNA of the structural information present in the coding sequences of the gene. The process includes, but is not limited to the following steps: (a) transcription initiation, (b) transcript elongation, (c) transcript splicing, (d) transcript capping, (e) transcript termination, (f) transcript polyadenylation, (g) nuclear export of the transcript, (h) transcript editing, and (i) stabilizing the transcript.

III.B. LH Polypeptides

The production and generation of wild-type and/or mutant LH polypeptides is also an aspect of the presently claimed subject matter. Such a wild-type or mutant polypeptide can comprise an LH polypeptide or a portion of an LH polypeptide, (e.g., an LH α or β subunit). Throughout the present disclosure it is intended that the term "mutant" encompass not only mutants of an LH polypeptide but chimeric proteins generated using an LH polypeptide as well. It is thus intended that the discussion of mutant LHs herein apply mutatis mutandis to chimeric LH polypeptides and to structural equivalents thereof.

In accordance with the presently claimed subject matter, a mutation can be directed to a particular site or combination of sites of a wild-type LH polypeptide. For example, a binding site can be chosen for mutagenesis. Similarly, a residue having a location on, at, or near the surface of the polypeptide can be replaced, resulting in an altered surface charge of one or more charge units as compared to the wild-type LH polypeptide. Alternatively, an amino acid residue in an LH polypeptide can be chosen for replacement based on its hydrophilic or hydrophobic characteristics.

Such mutants can be characterized by any one of several different properties as compared with the wild-type LH polypeptide. For example, such mutants can have an altered surface charge of one or more charge units, or can have an increase in overall stability. Other mutants can have altered substrate specificity in comparison with, or a higher specific activity than, a wild-type LH polypeptide.

LH mutants of the presently claimed subject matter can be generated in a number of ways. For example, the wild-type sequence of an LH polypeptide can be mutated at those sites identified using the presently claimed subject matter as desirable for mutation by employing oligonucleotide-directed mutagenesis or other conventional methods, such as deletion. Alternatively, mutants of an LH polypeptide can be generated by the site-specific replacement of a particular amino acid with an unnaturally occurring amino acid. In addition, LH mutants can be generated by replacement of an amino acid residue, for example, a particular cysteine or methionine residue, with selenocysteine or selenomethionine. This can be achieved by growing a host organism capable of expressing either the wild-type or mutant polypeptide on a growth medium depleted of either natural cysteine or methionine (or both) but enriched in selenocysteine or selenomethionine (or both).

Mutations can be introduced into a DNA sequence encoding an LH polypeptide using synthetic oligonucleotides. These oligonucleotides can contain nucleotide sequences flanking the desired mutation sites. Mutations can be generated in the full-length DNA sequence of an LH polypeptide or in any sequence encoding a polypeptide fragment of an LH polypeptide (e.g., an LH α or LH β subunit).

According to the presently claimed subject matter, a mutated LH DNA sequence produced by the methods described above, or any alternative methods known in the art, as well as wild-type LH sequences, can be expressed using an expression vector. An expression vector, as is well known to those of skill in the art, typically includes elements that permit autonomous replication in a host cell independent of the host genome, and one or more phenotypic markers for selection purposes. Either prior to or after insertion of the DNA sequences surrounding the desired LH coding sequence, an expression vector also will include control sequences encoding a promoter, operator, ribosome binding site, translation initiation signal, and, optionally, a repressor gene or various activator genes and a signal for termination. In some embodiments, where secretion of the encoded polypeptide is desired, nucleotides encoding a "signal sequence" can be inserted prior to and in frame with an LH coding sequence. For expression under the direction of the control sequences, a desired DNA sequence can be operatively linked to the control sequences; that is, the sequence can have an appropriate start signal in front of the DNA sequence encoding the LH polypeptide, and the correct reading frame to permit expression of that sequence under the control of the control sequences and production of the desired product encoded by that LH sequence must be maintained.

Any of a wide variety of well-known available expression vectors can be used to express LH coding sequences of the presently claimed subject matter. These expression vectors can be used in the techniques disclosed herein and can include, for example, vectors comprising segments of chromosomal, non-chromosomal, and synthetic DNA sequences, such as various known derivatives of SV40; known bacterial plasmids; e.g., plasmids from *E. coli* including ColE1, pCR1, pBR322, pMB9 and their derivatives; wider host range plasmids, e.g., RP4, phage DNAs, e.g., the numerous derivatives of phage λ, e.g., NM 989, and other DNA phages, e.g., M13 and filamentous single stranded DNA phages; yeast plasmids; and vectors derived from combinations of plasmids and phage DNAs, such as plasmids which have been modified to employ phage DNA or other expression control sequences. In one embodiment of the presently claimed subject matter, the *E. coli* vector pRSET A (Invitrogen Corp., Carlsbad, Calif., United States of America), including a T7-based expression system, is employed.

In addition, any of a wide variety of expression control sequences—sequences that control the expression of a DNA sequence when operatively linked to it—can be used in these vectors to express DNA sequences according to the presently claimed subject matter. Such useful expression control sequences, include, for example, the early and late promoters of SV40 for animal cells; the lac system, the trp system, the TAC or TRC system, the major operator and promoter regions of phage λ, and the control regions of fd coat protein, all for *E. coli*; the promoter for 3-phosphoglycerate kinase or other glycolytic enzymes; the promoters of acid phosphatase, e.g., Pho5; the promoters of the yeast α-mating factors for yeast; and other sequences known to control the expression of genes of prokaryotic or eukaryotic cells or their viruses, and various combinations thereof.

A wide variety of hosts are also useful for producing a mutated LH polypeptide according to the presently claimed subject matter. These hosts include, for example, bacteria, such as *E. coli, Bacillus*, and *Streptomyces*; fungi, such as yeasts; animal cells, such as Chinese hamster ovary (CHO) and COS-1 cells; plant cells; insect cells, such as Sf9 cells; and transgenic host cells.

It should be understood that not all expression vectors and expression systems function in the same way to express DNA sequences of the presently claimed subject matter and to produce LH polypeptides and/or LH mutants. Neither do all hosts function equally well with the same expression system. One of skill in the art can, however, make a selection among these vectors, expression control sequences, and hosts without undue experimentation and without departing from the scope of the presently claimed subject matter. For example, a consideration in selecting a vector is the ability of the vector to replicate in a given host. The copy number of the vector, the ability to control that copy number, and the expression of any other proteins encoded by the vector, such as antibiotic markers, can also be considered.

In selecting an expression control sequence, a variety of factors should also be considered. These include, for example, the relative strength of the system, its controllability, and its compatibility with the DNA sequence encoding an LH polypeptide of the presently claimed subject matter, with particular regard to the formation of potential secondary and tertiary structures.

Hosts should be selected by consideration of their compatibility with the selected vector, the toxicity of an LH polypeptide to them, their ability to express mature products, their ability to fold proteins correctly, their fermentation requirements (if any), the ease of purification of a modified LH polypeptide, and safety. Within these parameters, one of skill in the art can select various vector/expression control system/host combinations that will produce useful amounts of an LH polypeptide.

A mutant LH polypeptide produced in these systems can be purified by a variety of conventional steps and strategies, including those used to purify the wild-type LH polypeptide. Once an LH mutation has been generated in the desired location, the mutants can be tested for any one of several properties of interest. For example, mutants can be screened for an altered charge at physiological pH. This can be determined by measuring the mutant LH polypeptide's isoelectric point (pI) and comparing the observed value with that of the wild-type parent. Isoelectric points can be measured by gel-electrophoresis according to the method of Wellner (Wellner, (1971) *Anal. Chem.* 43: 597). A mutant LH polypeptide containing a replacement amino acid located at the surface of the enzyme, as provided by the structural information of the presently claimed subject matter, can lead to an altered surface charge and an altered pI.

Thus, in another aspect of the presently claimed subject matter, a mutant LH polypeptide can be generated. Such a mutant can, for example, facilitate purification and can also facilitate the study and/or therapeutic use of one or more biological activities of an LH polypeptide.

As used in the following discussion, the terms "engineered LH" and "LH mutant" are used interchangeably and refer to polypeptides having amino acid sequences that contain at least one mutation in the wild-type sequence. The terms also refer to LH polypeptides that are capable of exerting a biological effect in that they comprise all or a part of the amino acid sequence of an LH mutant polypeptide of the presently claimed subject matter, or cross-react with antibodies raised against an LH mutant polypeptide, or retain all or some or an enhanced degree of the biological activity of an LH mutant amino acid sequence or protein. Such biological activity can include association with a Leydig cell as well as enhancing serum testosterone levels.

The terms "engineered LH" and "LH mutant" also include analogs of an LH mutant polypeptide. By "analog" is intended that a DNA or polypeptide sequence can contain alterations relative to the sequences disclosed herein, yet retain all or some or an enhanced degree of the biological activity of those sequences. Analogs can be derived from genomic nucleotide sequences or from other organisms, or can be created synthetically. Those of skill in the art will appreciate that other analogs, as yet undisclosed or undiscovered, can be used to design and/or construct LH mutant analogs. There is no need for an LH mutant polypeptide to comprise all or substantially all of the amino acid sequence of SEQ ID NOs: 2, 4, or 6. Shorter or longer sequences are anticipated to be of use in the presently claimed subject matter; shorter sequences are herein referred to as "segments". Thus, the terms "engineered LH" and "LH mutant" also include fusion, chimeric, or recombinant LH mutant polypeptides and proteins comprising sequences of the presently claimed subject matter. Methods of preparing such proteins are disclosed herein above and are known to those of ordinary skill in the art.

III.C. Sequences that are Substantially Identical to a Wild Type or LH Mutant Sequence Nucleic acids that are substantially identical to a nucleic acid sequence of a wild type LH or an LH mutant of the presently claimed subject matter, e.g., allelic variants, genetically altered versions of the gene, etc., bind to a wild type or a mutant LH sequence under stringent hybridization conditions. By employing probes, particularly labeled probes of DNA sequences, one can isolate homologous or related genes. The source of homologous genes can be any species, e.g., primate species; rodents, such as rats and mice; canines; felines; bovines; equines; yeast; nematodes; etc.

Between mammalian species, e.g., human and mouse, homologs have substantial sequence similarity, typically at least about 75% sequence identity between nucleotide sequences. Sequence identity is calculated based on a reference sequence, which can be a subset of a larger sequence, such as a conserved motif, coding region, flanking region, etc. A reference sequence will usually be at least about 18 nucleotides (nt) long, more commonly at least about 30 nt long, and can extend to the complete sequence that is being compared. Algorithms for sequence analysis are known in the art, such as BLAST, described in Altschul et al., (1990) *J. Mol. Biol.* 215: 403-10.

Percent identity or percent similarity of a DNA or peptide sequence can be determined, for example, by comparing sequence information using the GAP computer program, available from Accelrys, Inc. (San Diego, Calif., United States of America). The GAP program employs the alignment method of Needleman & Wunsch, (1970) *J. Mol. Biol.* 48: 443, as revised by Smith & Waterman, (1981) *Adv. Appl. Math.* 2:482. Briefly, the GAP program defines similarity as the number of aligned symbols (i.e., nucleotides or amino acids) that are similar divided by the total number of symbols in the shorter of the two sequences. Representative parameters for the GAP program are the default parameters, which do not impose a penalty for end gaps. See, e.g., Schwartz et al. (eds.), (1979), *Atlas of Protein Sequence and Structure, National Biomedical Research Foundation*, pp. 357-358, and Gribskov et al., (1986) *Nucl. Acids. Res.* 14: 6745.

As used herein, DNA analog sequences are "substantially identical" to specific DNA sequences disclosed herein if: (a) the DNA analog sequence is derived from coding regions of the nucleic acid sequence shown in SEQ ID NOs: 1, 3, and 5; or (b) the DNA analog sequence is capable of hybridization with DNA sequences of (a) under stringent conditions and which encode a biologically active LH gene product; or (c) the DNA sequences are degenerate as a result of alternative genetic code to the DNA analog sequences defined in (a) and/or (b). Substantially identical analog proteins and nucleic acids will have in one embodiment between about 70% and 80%, in another embodiment between about 80% to about 90%, and in still another embodiment between about 90% and 99% sequence identity with the corresponding sequence of the native protein or nucleic acid. Sequences having lesser degrees of identity but comparable biological activity are considered to be equivalents.

As used herein, the term "stringent conditions" refers to conditions of high stringency, for example 6×SSC, 0.2% polyvinylpyrrolidone, 0.2% Ficoll, 0.2% bovine serum albumin, 0.1% sodium dodecyl sulfate, and 100 µg/ml salmon sperm DNA, at 68° C. For the purposes of specifying additional conditions of high stringency, representative conditions are a salt concentration of about 200 mM and a temperature of about 45° C. One example of such stringent conditions is hybridization at 4×SSC at 65° C., followed by a washing in 0.1×SSC at 65° C. for one hour. Another exemplary stringent hybridization scheme uses 50% formamide, 4×SSC at 42° C.

III.C.1. Complementarity and Hybridization to a Wild Type or a Mutant LH Sequence As used herein, the term "complementary sequences" refers to nucleic acid sequences that are base-paired according to the standard Watson-Crick complementarity rules. The presently claimed subject matter also encompasses the use of nucleotide segments that are complementary to the sequences of the presently claimed subject matter.

Hybridization can also be used to assess complementary sequences and/or to isolate complementary nucleotide sequences. As discussed above, nucleic acid hybridization is affected by such conditions as salt concentration, temperature, or organic solvents, in addition to the base composition, length of the complementary strands, and the number of nucleotide base mismatches between the hybridizing nucleic acids, as is readily appreciated by those skilled in the art. Stringent temperature conditions generally include temperatures in one embodiment in excess of about 30° C., in another embodiment in excess of about 37° C., and in still another embodiment in excess of about 45° C. Stringent salt conditions are in one embodiment less than about 1,000 mM, in another embodiment less than about 500 mM, and in still another embodiment less than about 200 mM. However, the combination of parameters is much more important than the measure of any single parameter. See, e.g., Wetmur & Davidson, (1968) *J. Mol. Biol.* 31:349-70. Determining appropriate hybridization conditions to identify and/or isolate sequences containing high levels of homology is well known in the art. See, e.g., Sambrook & Russell, (2001) *Molecular Cloning: A Laboratory Manual*, Cold Spring Harbor Laboratory Press, Cold Spring Harbor, N.Y., United States of America.

III.C.2. Functional Equivalents of a Wild Type or a Mutant LH Nucleic Acid Sequence As used herein, the term "functionally equivalent codon" is used to refer to codons that encode the same amino acid, such as the ACG and AGU codons for serine. LH-encoding nucleic acid sequences comprising SEQ ID NOs: 1, 3, or 5 that have functionally equivalent codons are covered by the presently claimed subject matter. Thus, when referring to the sequence examples presented in SEQ ID NOs: 2, 4, and 6, substitution of functionally equivalent codons into the sequence examples of SEQ ID NOs: 1, 3, and 5 is also provided. Thus, the inventor is in possession of amino acid and nucleic acids sequences that include such substitutions, but are not set forth herein in their entirety for convenience.

It will also be understood by those of skill in the art that amino acid and nucleic acid sequences can include additional residues, such as additional N- or C-terminal amino acids or 5' or 3' nucleic acid sequences, and yet still be essentially as set forth in one of the sequences disclosed herein, so long as the sequence retains biological activity with respect to polypeptide expression. The addition of terminal sequences particularly applies to nucleic acid sequences that can, for example, include various non-coding sequences flanking either of the 5' or 3' portions of the coding region or can include various internal sequences (for example, introns) that are known to occur within genes.

III.C.3. Biological Equivalents

The presently claimed subject matter envisions and includes biological equivalents of a wild type or a mutant LH polypeptide of the presently claimed subject matter. The term "biological equivalent" refers to proteins having amino acid sequences that are substantially identical to the amino acid sequence of a wild type or a mutant LH of the presently claimed subject matter and that are capable of exerting a biological effect in that they are capable of associating with a Leydig cell or crossreacting with anti-LH mutant antibodies raised against a wild type or an LH polypeptide of the presently claimed subject matter.

For example, certain amino acids can be substituted for other amino acids in a protein structure without appreciable loss of interactive capacity with, for example, structures on the surface of a Leydig cell. Since it is the interactive capacity and nature of a protein that defines that protein's biological functional activity, certain substitutions can be made in a protein sequence (or the nucleic acid sequence encoding it) to obtain a protein with the same, enhanced, or antagonistic properties. Such properties can be achieved by interaction with the normal targets of the protein, but this need not be the case, and the biological activity of the presently claimed subject matter is not limited to a particular mechanism of action. It is thus in accordance with the presently claimed subject matter that various changes can be made in the amino acid sequence of a wild type or a mutant LH polypeptide of the presently claimed subject matter or its underlying nucleic acid sequence without appreciable loss of biological utility or activity.

Biologically equivalent polypeptides, as used herein, are polypeptides in which certain, but not most or all, of the amino acids can be substituted. Thus, when referring to the sequence examples presented in SEQ ID NOs: 2, 4, and 6, applicant envisions substitution of codons that encode biologically equivalent amino acids, as described herein, into the sequence examples of SEQ ID NOs: 1, 3, and 5. Thus, the inventor is in possession of amino acid and nucleic acids sequences which include such substitutions but which are not set forth herein in their entirety for convenience.

Alternatively, functionally equivalent proteins or peptides can be created via the application of recombinant DNA technology, in which changes in the protein structure can be engineered based on considerations of the properties of the amino acids being exchanged, e.g., substitution of Ile for Leu. Changes designed by man can be introduced through the application of site-directed mutagenesis techniques, for example, to introduce improvements in the antigenicity of the protein or to test a wild type or a mutant LH polypeptide of the presently claimed subject matter for its ability to associate with a Leydig cell, or other activity, at the molecular level.

Amino acid substitutions, such as those that might be employed in modifying a wild type or a mutant LH polypeptide of the presently claimed subject matter are generally, but not necessarily, based on the relative similarity of the amino acid side-chain substituents, for example, their hydrophobicity, hydrophilicity, charge, size, and the like. An analysis of the size, shape, and type of the amino acid side-chain substituents reveals that arginine, lysine, and histidine are all positively charged residues; that alanine, glycine, and serine are all of similar size; and that phenylalanine, tryptophan, and tyrosine all have a generally similar shape. Therefore, based upon these considerations, arginine, lysine, and histidine; alanine, glycine, and serine; and phenylalanine, tryptophan, and tyrosine are defined herein as biologically functional equivalents. Other biologically functionally equivalent changes will be appreciated by those of ordinary skill in the art. It is implicit in the above discussion, however, that one of skill in the art can appreciate that a radical, rather than a conservative substitution can be warranted in a given situation. Non-conservative substitutions in a wild type or a mutant LH polypeptide of the presently claimed subject matter are also an aspect of the presently claimed subject matter.

In making biologically functional equivalent amino acid substitutions, the hydropathic index of amino acids can be considered. Each amino acid has been assigned a hydropathic index on the basis of their hydrophobicity and charge characteristics. The assigned hydropathic indices are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9);

tyrosine (−1.3); proline (−1.6); histidine (−3.2); glutamic acid (−3.5); glutamine (−3.5); aspartic acid (−3.5); asparagine (−3.5); lysine (−3.9); and arginine (−4.5).

The importance of the hydropathic amino acid index in conferring interactive biological function on a protein is generally understood in the art (Kyte & Doolittle, (1982), *J. Mol. Biol.* 157: 105-132, incorporated herein by reference). It is known that certain amino acids can be substituted for other amino acids having a similar hydropathic index or score and still retain a similar biological activity. In making changes based upon the hydropathic index, the substitution of amino acids whose hydropathic indices can be in one embodiment within ±2 of the original value, in another embodiment within ±1 of the original value, and in still another embodiment within ±0.5 of the original value.

It is also understood in the art that the substitution of like amino acids can be made effectively on the basis of hydrophilicity. U.S. Pat. No. 4,554,101 to Hopp, incorporated herein by reference, states that the greatest local average hydrophilicity of a protein, as governed by the hydrophilicity of its adjacent amino acids, correlates with its immunogenicity and antigenicity; that is, with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4).

In making changes based upon similar hydrophilicity values, the substitution of amino acids whose hydrophilicity values can be in one embodiment within ±2 of the original value, in another embodiment within ±1 of the original value, and in still another embodiment within ±0.5 of the original value.

While the foregoing discussion has focused on functionally equivalent polypeptides arising from amino acid changes, it will be appreciated that these changes can be effected by alteration of the encoding DNA, taking into consideration also that the genetic code is degenerate and that two or more codons can code for the same amino acid.

Thus, it will also be understood that the presently claimed subject matter is not limited to the particular amino acid and nucleic acid sequences of SEQ ID NOs: 1-6. Recombinant vectors and isolated DNA segments can therefore variously include a wild type or an engineered LH polypeptide-encoding region itself, include coding regions bearing selected alterations or modifications in the basic coding region, or include larger polypeptides which nevertheless comprise LH polypeptide-encoding regions or encode biologically functional equivalent proteins or polypeptides which have variant amino acid sequences. A biological activity of a wild type or an engineered LH polypeptide can be determined, for example, by ligand binding assays known to those of skill in the art.

The nucleic acid segments of the presently claimed subject matter, regardless of the length of the coding sequence itself, can be combined with other DNA sequences, such as promoters, enhancers, polyadenylation signals, additional restriction enzyme sites, multiple cloning sites, other coding segments, and the like, such that their overall length of the nucleic acid segments can vary considerably. It is therefore contemplated that a nucleic acid segment of almost any length can be employed, with the total length being limited in one embodiment by the ease of preparation and use in the intended recombinant DNA protocol. For example, nucleic acid fragments can be prepared that include a short stretch complementary to a nucleic acid sequence set forth in SEQ ID NOs: 1, 3, or 5, such as about 10 nucleotides, and which are up to 10,000 or 5,000 base pairs in length. DNA segments with total lengths of about 4,000, 3,000, 2,000, 1,000, 500, 200, 100, and about 50 base pairs in length can also be used.

The DNA segments of the presently claimed subject matter encompass biologically functional equivalents of a wild type or an engineered LH polypeptide. Such sequences can arise as a consequence of codon redundancy and functional equivalency that are known to occur naturally within nucleic acid sequences and the proteins thus encoded. Alternatively, functionally equivalent proteins or polypeptides can be created via the application of recombinant DNA technology, in which changes in the protein structure can be engineered based on considerations of the properties of the amino acids being exchanged. Changes can be introduced through the application of site-directed mutagenesis techniques, e.g., to introduce improvements in the antigenicity of the protein or to test variants of a wild type or a mutant LH of the presently claimed subject matter in order to examine the degree of ligand binding activity, or other activity at the molecular level. Various site-directed mutagenesis techniques are known to those of skill in the art and can be employed in the presently claimed subject matter.

The presently claimed subject matter further encompasses fusion proteins and peptides wherein a wild type or a mutant LH coding region of the presently claimed subject matter is aligned within the same expression unit with other proteins or peptides having desired functions, such as for purification or immunodetection purposes.

Recombinant vectors form important further aspects of the presently claimed subject matter. Particularly useful vectors are those in which the coding portion of the DNA segment is positioned under the control of (i.e., operatively linked to) a promoter. The promoter can be that naturally associated with an LH gene, as can be obtained by isolating the 5' non-coding sequences located upstream of the coding segment or exon, for example, using recombinant cloning and/or PCR technology and/or other methods known in the art, in conjunction with the compositions disclosed herein.

In other embodiments, certain advantages will be gained by placing the coding DNA segment under the control of a recombinant, or heterologous, promoter. As used herein, a recombinant or heterologous promoter is a promoter that is not normally associated with an LH gene in its natural environment. Such promoters can include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology (see, e.g., Sambrook & Russell, (2001) *Molecular Cloning: A Laboratory Manual*, Cold Spring Harbor Laboratory Press, Cold Spring Harbor, N.Y., United States of America, specifically incorporated herein by reference). The promoters employed can be constitutive or inducible, and can be used under the appropriate conditions to direct high level expression of the introduced DNA segment, such as is advantageous in the large-scale production of recombinant proteins or peptides. One exemplary promoter system contemplated for use in high-level expression is a T7 promoter-based system.

III.D. Analogs of T3 and T4

Some aspects of the presently claimed subject matter employ thyroid hormones, including T3 and T4. These small molecules comprise the chemical structures presented hereinabove. However, the methods of the presently claimed subject matter are not limited to the chemical structures disclosed. The presently claimed subject matter encompasses modifications to the disclosed structures. Thus, the terms "T3" and "T4" include structures that are designed using the disclosed chemical structures of T3 and T4 as a starting point. T3 and T4 molecules can be modified to alter one or more properties, such as solubility, bioavailability, or binding, using methods known to those of ordinary skill in the art.

For example, various computer-based modeling programs, such as those described herein, can assist in predicting the binding of T3 and T4 to a receptor, such as those found on the surface of Leydig cells. Upon discovering that such binding in fact takes place, knowledge of the protein structure then allows design and synthesis of one or more ligands that mimic the functional binding of T3 and T4. This is the method of "rational" drug design, further described herein.

Use of the structures of the presently claimed subject matter, independently or in conjunction with one another structure, in a rational ligand design process is thus provided in accordance with the presently claimed subject matter. Several rational ligand design techniques are described in U.S. Pat. Nos. 5,834,228 to Becker et al. and 5,872,011 to Burley et al., incorporated herein in their entireties.

Thus, in addition to T3 and T4, other sterically similar compounds can be formulated to interact with a key structural region of a T3 or T4 receptor. The generation of a structural functional equivalent can be achieved by the techniques of modeling and chemical design known to those of ordinary skill in the art and described herein. It will be understood that all such sterically similar constructs fall within the scope of the presently claimed subject matter.

The design of T3 and T4 analogs can be facilitated by conventional ball and stick type modeling procedures. However, it is contemplated that the ability to design analogs can be enhanced significantly by employing modern computer-driven modeling and design procedures.

The design of T3 and T4 analogs can be facilitated by employing conventional molecular modeling computers or workstations, commercially available from, for example, Silicon Graphics, Inc. (Mountain View, Calif., United States of America) or Evans & Sutherland Computer Corp. (Salt Lake City, Utah, United States of America), which implement equally conventional computer modeling programs, for example, INSIGHT II™, DISCOVER™, and DELPHI™, which are commercially available from Biosym Technologies Inc. (San Diego, Calif., United States of America), and QUANTA™ and CHARMM™, commercially available from Molecular Simulations, Inc. (San Diego, Calif., United States of America).

With respect to T3 or T4, for example, upon identification of chemical groups of interest, a skilled artisan using a conventional computer program can design a small molecule having desired chemical moieties disposed upon a suitable carrier framework. Useful computer programs include CONCORD™, MOGLI™, MACROMODEL™ and BIOGRAPHO™. These and other software packages are described in, for example, Dixon, (1992) *Trends Biotechnol.* 10: 357-363; Tschinke et al., (1993) *J. Med. Chem.* 36: 3863-3870; Eisen et al., (1994) *Proteins* 19: 199-221; *Computer Aided Drug Design*, (1989) (Perun & Propst, eds.), Marcel-Dekker, Inc., New York, N.Y., United States of America, pp. 2-4; Hopfinger, (1985) *J. Med. Chem.* 28: 1133-1139; Cohen et al., (1990) *J. Med. Chem.* 33: 883-894, the disclosures of which are incorporated herein by reference.

One particular computer program entitled CAVEAT™ searches a database, for example, the Cambridge Structural Database, for structures that have desired spatial orientations of chemical moieties (Bartlett et al., (1989) in *Molecular Recognition: Chemical and Biological Problems* (Roberts, ed.) pp. 182-196). The CAVEAT™ program has been used to design analogs of tendamistat, a 74 residue inhibitor of α-amylase, based on the orientation of selected amino acid side chains in the three-dimensional structure of tendamistat (Bartlett et al., (1989) in *Molecular Recognition: Chemical and Biological Problems* (Roberts, ed.) pp 182-196).

Alternatively, upon identification of a series of analogs which mimic the biological activity of T3 or T4 (which can be determined by in vivo or in vitro assays), the skilled artisan can use a variety of computer programs to develop quantitative structure activity relationships (QSAR) and further to assist in the de novo design of T3 and T4 analogs. Other useful computer programs are described in, for example, Connolly-Martin, (1991) *Method Enzymol.* 203: 587-613; Dixon, (1992) *Trends Biotechnol.* 10: 357-363; and Waszkowycz et al., (1994) *J. Med. Chem.* 37: 3994-4002.

In another aspect of the presently claimed subject matter, a T3 or T4 derivative can generally be prepared as follows: (a) providing a molecular model of T3 or T4; (b) identifying a candidate analog known or suspected to have a three dimensional shape corresponding to the three dimensional shape representative of at least a portion of T3 or T4; and (c) producing the candidate analog identified in step (b). This approach is presented purely for illustrative purposes and those of ordinary skill in the art will recognize variations on this approach, upon consideration of the present disclosure.

Summarizing, the above methods can be employed to design a molecule with an alteration in a property of the molecule (e.g., greater biological activity) by employing a series of model refinement steps. For example, a two or three-dimensional model of a T3 molecule can be considered and a modification to the structure proposed. The structural modification can be made to the structure and the effect of the modification can be evaluated in an in vivo or in vitro system, which can comprise an evaluation of the effect each structure has on, for example, Leydig cell rejuvenation and/or a serum testosterone level. This process can be repeated a desired number of times with a different structural modification being introduced with each iteration.

Thus, when T3 or T4 is employed as a starting material for compounds designed to enhance Leydig cell rejuvenation and/or elevate serum testosterone levels, all resulting engineered compounds are considered to be encompassed by the terms "T3" and "T4", as those terms are employed in the specification and claims of the present disclosure.

The foregoing discussion is equally applicable to analogs, derivatives, and functional equivalents of one of T3 and T4 that are designed, developed, or synthesized via another approach. Such analogs, derivatives, and functional equivalents also fall within the scope of the presently claimed subject matter.

IV. REJUVENATING LEYDIG CELLS AND ENHANCING A SERUM TESTOSTERONE LEVEL

In one aspect of the presently claimed subject matter, Leydig cells can be rejuvenated in vivo. Rejuvenation of Leydig cells in an aged subject, for example, can result in Leydig cell function at a level comparable to that of a much younger subject. In another aspect of the presently claimed subject matter, a serum testosterone level can be elevated to a desired level. In an aged subject, a desired serum testosterone level can be that normally found in a non-aged subject. By way of particular example, a desired serum testosterone level can be that found in a normal healthy human male, in one embodiment, at least about 250 ng/100 ml and in another embodiment ranging from about 250 ng/100 ml to about 1250 ng/100 ml. These applications of the presently claimed subject matter are discussed further hereinbelow.

IV.A. Rejuvenating Leydig Cells

In one aspect of the presently claimed subject matter, a method for rejuvenating Leydig cells in a male subject having Leydig cells is disclosed. In one embodiment, the method comprises (a) providing a male subject having Leydig cells; and; (b) coadministering luteinizing hormone (LH) and thyroid hormone (TH) to the subject, whereby rejuvenation of Leydig cells in the subject is accomplished.

In this aspect of the presently claimed subject matter, a male subject is initially provided. In one embodiment, the subject is a mammal, and in another embodiment the subject is a human male, however the disclosed methods can be applied to any mammal. The subject can also have atrophied Leydig cells. Leydig cell atrophy accompanies advancing age, with a concomitant decrease in serum levels of testosterone. Thus, in a subject undergoing andropause, decreased testosterone levels correlate with the degree of Leydig cell atrophy.

LH and TH can then be coadministered to a subject. In one embodiment, the TH is T4. However, T3 or another TH can also be employed. These two compounds can be administered in a variety of ways. For example, an osmotic pump can be implanted in a subject. Generally, osmotic pumps, such as an ALZET® pump available from Durect Corporation (Cupertino, Calif., United States of America), employ osmotic pressure to release a drug disposed in the pump at constant and regular timepoints. In a typical design, the pump comprises three chambers: a salt chamber containing excess solid salt, a drug chamber, and a water chamber. The salt and water compartments are separated by a rigid membrane permeable to water but impermeable to ionized and hydrated salt ions. An elastic diaphragm separates the salt and drug chambers. In operation, water is imbibed osmotically into the salt chamber, causing the elastic diaphragm to expand into the drug chamber and forcing the drug out through the delivery orifice. Depending on the salt used, the osmotic pressure developed by this type of pump is usually between 50 and 200 atmospheres. The pressure required to pump the drug from the device is small in comparison, and hence the drug delivery rate remains constant as long as some excess undissolved salt remains in the salt chamber. See Theeuwes & Yum, (1976) *Ann. Biomed. Eng.* 4(4): 343-353.

In one embodiment, the pump is implanted subdermally in the tissue of the subject. The pump can be programmed to regularly dispense a predetermined metered dose of each of LH and TH at a desired time. In some cases, it can be desirable to implant the pump for chronic, long-term treatment. A wide range of implantable pumps is commercially available. Suitable implantable pumps include the ALZET® pump, available from Durect Corporation (Cupertino, Calif., United States of America). Controlled release devices can also be employed, such as the DUROS® device available from Alza Corporation (Mountain View, Calif., United States of America).

LH and/or TH can also be coadministered to a subject via a transdermal delivery system. Transdermal delivery of various drugs and pressure sensitive adhesive matrix patches for transdermal delivery of such drugs are known in the art of drug delivery. These matrix patches include a pressure sensitive adhesive layer for affixing the patch to the skin and for carrying the drug and any excipients that are directly incorporated into this adhesive layer. These adhesive matrix patches also typically include an inert, impervious backing layer and a release liner that is peeled off and discarded before applying the patch to the skin. These patches are distinguished from reservoir patches in that the drug in a reservoir patch is incorporated in a layer or compartment separate from the pressure sensitive adhesive layer. An example of a reservoir transdermal patch is described in U.S. Pat. No. 5,120,546 to Hansen et al. The transdermal route of parenteral delivery of drugs and other biologically active agents has been proposed for a wide variety of systemically acting and locally acting agents on either a rate-controlled or non-rate-controlled basis and is described in numerous technical publications such as the following: U.S. Pat. Nos. 3,598,122; 3,598,123; 3,731,683; 3,797,494; 4,031,894; 4,201,211; 4,286,592; 4,314,557; 4,379,454; 4,435,180; 4,559,222; 4,568,343; 4,573,995; 4,588,580; 4,645,502; 4,704,282; 4,788,062; 4,816,258; 4,849,226; 4,908,027; 4,943,435; and 5,004,610, the disclosures of which are incorporated in their entireties herein by reference.

U.S. Pat. No. 6,132,760 to Hedenstrom, incorporated herein, discloses a transdermal system for delivering testosterone to a patient; a system such as this can also be employed to deliver LH and/or TH to a patient in the presently claimed subject matter. U.S. Pat. No. 6,274,165 to Meconi et al., incorporated herein by reference, discloses a transdermal, hormone-delivering therapeutic system. Similarly, U.S. Pat. No. 5,985,311 to Cordes et al., also incorporated herein by reference, discloses a transdermal hormone patch. Both of these prior art systems can be employed in the presently claimed subject matter to administer LH and/or TH to a subject. Transdermal delivery systems offer the advantage that the system can be implanted in or on the skin of a patient without the need to perform surgery or other invasive procedure. Of course, osmotic pumps as disclosed herein can be employed with a transdermal delivery system as disclosed herein.

LH and TH can be provided to a subject in a variety of forms. It is noted again that TH specifically encompasses T3 and T4, as well as analogs and functional equivalents thereof, as disclosed herein above. In one embodiment, T4 is employed in the presently claimed subject matter, although T3 can also be employed. For example, LH and TH can be prepared in a single formulation, such as phosphate buffered saline. This formulation can be placed in an implantable pump and administered to a subject according to a predetermined regular schedule. Alternatively, separate pumps can be employed to release a desired dosage of each of TH and LH at regular predetermined intervals. The pumps can operate independently from one another or can be configured to communicate with one another. As disclosed hereinabove and in the Examples, co-administration of LH and TH to a subject in need thereof (in one embodiment, an aged mammalian male) has the effect of rejuvenating the subject's Leydig cells.

IV.B. Enhancing a Serum Testosterone Level

There are several pharmaceutical methods presently available to restore testosterone levels in humans with suboptimal levels. Many of these have disadvantages, however. For example, testosterone esters have been used as injections for decades, however these injections can be inconvenient and often painful. Additionally, these injections can also result in inconsistent blood levels as a supraphysiological surge is seen soon after injection, but by the time the next injection is due, the levels have often dropped down below standard physiological levels. This is in contrast with testosterone levels under normal conditions, which are quite stable within mild release pulses of approximately 90 minute duration. Supraphysiological surges that are seen with injectable preparations can increase the incidence of undesirable side effects (e.g., prostrate hypertrophy) as well as cause an amplified shutdown of the hypothalamic/pituitary testicular axis (HPTA).

Other pharmaceutical methods for androgen replacement therapy include synthetic oral androgen derivatives. These types of compounds (e.g., methyltestosterone and fluoxymesterone) are altered in the 17-alpha position of the steroid molecule with an alkyl group. This alkyl group renders the steroid impervious to oxidation of the 17-β hydroxyl group in the liver and therefore greatly improves its oral bioavailability compared to the non-alkylated steroids. However, this structural modification also has been associated with a greatly increased risk of hepatotoxicity. Therefore, these synthetic compounds are not a viable solution.

It is noted that the seminiferous tubules can produce a small amount of testosterone given the proper precursor compounds (e.g., progesterone). The extent of testosterone produced via this pathway is extremely small in comparison with the production of testosterone by Leydig cells.

The presently claimed subject matter discloses an alternative to these direct therapy approaches. Rather than injecting testosterone directly into a subject, the presently claimed subject matter comprises coadministering LH and TH to a subject in order to effect an elevation of serum testosterone levels. This approach offers many advantages over prior art approaches, including the minimization of undesirable and potentially hazardous side effects.

In one embodiment of the presently claimed subject matter, an effect of rejuvenating the Leydig cells of an aged mammalian male is an enhancement in the serum levels of testosterone in the subject. As discussed hereinabove, Leydig cells comprise one site for the synthesis of sex steroids and hormones, including testosterone. When Leydig cells are at their most active, which occurs in younger or non-aged males, testosterone production by these cells is at its highest.

In one aspect of the presently claimed subject matter, a method of enhancing testosterone production in a male subject is disclosed. In one embodiment, the method comprises: (a) providing a male subject having Leydig cells and a serum testosterone level less than a desired level; and (b) coadministering luteinizing hormone (LH) and thyroid hormone (TH) to the subject, whereby testosterone production in the subject is enhanced.

In this aspect of the presently claimed subject matter, a male subject having Leydig cells and a serum testosterone level less than a desired level is provided. In one embodiment, the subject is a mammal, and in another embodiment, the subject is a human. The subject can also be an aged male subject. An aged subject might want to increase testosterone production by a Leydig cell to a level found in a healthy younger subject. Testosterone production can be elevated to virtually any safe level a subject desires, within the bounds set by the normal physiology of the subject. Normal testosterone production in a healthy human male gives a serum testosterone level of about 250 ng/100 ml to about 1250 ng/100 ml. Thus, a desired serum testosterone level can be in one embodiment about 250 ng/100 ml, in another embodiment about 350 ng/100, in another embodiment about 450 ng/100 ml, in another embodiment about 550 ng/100 ml, in another embodiment about 650 ng/100 ml, in another embodiment about 750 ng/100 ml, in another embodiment about 850 ng/100 ml, in another embodiment about 950 ng/100 ml, in another embodiment about 1050/100 ml, in another embodiment about 1150 ng/100 ml, and in still another embodiment about 1250 ng/100 ml, as well as ranges therein.

There are many circumstances for which it might be desirable to elevate testosterone levels in a subject. As is commonly known to those of skill in the art, and as discussed herein, testosterone levels play a critical role in reproduction. However, testosterone has also been implicated in a range of other pathways and systems in the male. For example, organ systems in which testosterone levels are important include the brain (for libido and mood), skin (for hair growth and sebaceous gland activity), muscle (to increase muscle strength and volume), liver (to synthesize serum proteins) synovial tissue (to modulate immune responses), bone (to maintain strength and volume), bone marrow (to stimulate stem cells) and kidney (to stimulate erythropoietin). (see Morales et al., (1996) *Int. J. Impotence Res.* 8:95-97; Norman et al., (1993) *Hormones*, Academic Press, New York, N.Y., United States of America, pp. 169-191; Anderson et al., (1996) *Bone* 18:171-177; Gobien, *Br. J. Urol.* 78:763-768.) Thus, there are a number of circumstances under which it might be desirable to increase testosterone in a subject.

In another aspect of the presently claimed subject matter, a decreased testosterone level is due to Leydig cell atrophy. Leydig cell atrophy is a physiological process that occurs in males as they age. The most significant effects of Leydig cell atrophy are normally observed in human males over the age of 50. It is noted, however, that Leydig cell atrophy is a chronic process that can begin as early as the late twenties or early thirties. The treatment of such a subject is provided in accordance with the presently claimed subject matter.

After providing an aged mammalian male subject with testosterone production that is decreased to a level less than a desired level due to Leydig cell atrophy, the subject is treated with LH and TH. More specifically, LH and TH are coadministered to the subject. The administration can be made using any of a range of technologies, some of which are described hereinabove. In one embodiment, one or more osmotic pumps are implanted in the tissue of a subject. In one embodiment, the pumps are implanted in the tissue of the subject's body, although those of ordinary skill in the art will recognize other appropriate sites for placement of the pump(s). LH and/or TH can also be administered to a subject via a transdermal system, such as those disclosed hereinabove.

V. TREATING ANDROPAUSE

Andropause is related to a decrease in serum hormone levels in males, including testosterone levels, which accompanies aging. In human males, andropause can begin in the early forties. One factor that contributes to andropause is atrophy of the Leydig cells.

In one aspect, the presently claimed subject matter discloses a method of treating andropause in an aged male subject having Leydig cells. In this embodiment of the presently claimed subject matter the method comprises: (a) providing an aged male subject having Leydig cells and undergoing andropause; and (b) coadministering luteinizing hormone (LH) and thyroid hormone (TH) to the subject, whereby andropause is treated in an aged male subject having Leydig cells.

In this aspect of the presently claimed subject matter, an aged male subject having Leydig cells and undergoing andropause is provided. In one embodiment, the subject is a mammal, and in another embodiment, the subject is a human.

Since in humans andropause typically begins in the early forties to early fifties, in one embodiment a human subject is older than forty years of age.

LH and TH are then coadministered to the subject. These compounds can be administered via the methods and apparatuses discussed hereinabove. For example, LH and TH can be administered by an osmotic pump, as disclosed hereinabove, and/or by another device, such as a transdermal system, as disclosed hereinabove.

Therefore, the presently claimed subject matter comprises an alternative to androgen therapy for minimizing the effects of androgen deficiency during age advancement.

VI. CORRELATION OF DATA OBTAINED IN BROWN NORWAY RATS TO HUMANS

The Brown Norway rat was chosen for this study because this strain has been recommended as a suitable model for male reproductive aging studies (Wang et al., (1993) *Endocrinol.* 133:2773-2781 and Zirkin et al., (1993) *J. Androl.* 14:118-123).

VII. CONCLUSIONS

The presently claimed subject matter discloses the ability to rejuvenate Leydig cells. The rejuvenation is accomplished, in part, by coadministering LH and TH to a subject. In another aspect of the presently claimed subject matter, a serum testosterone level in a subject can be raised to a desired level. This can also be accomplished, in part, by coadministering TH and LH to the subject. Further, the presently claimed subject matter can be employed in the treatment of andropause. Summarily, the presently claimed subject matter can be employed to "reverse" aging and andropause in a subject by rejuvenating Leydig cells and raising serum testosterone levels to a desired level.

EXAMPLES

The following Examples have been included to illustrate exemplary modes of the presently claimed subject matter. Certain aspects of the following Examples are described in terms of techniques and procedures found or contemplated by the present inventor to work well in the practice of the presently claimed subject matter. These Examples are exemplified through the use of standard practices of the inventor. In light of the present disclosure and the general level of skill in the art, those of skill will appreciate that the following Examples are intended to be exemplary only and that numerous changes, modifications, and alterations can be employed without departing from the spirit and scope of the presently claimed subject matter.

An object of Examples 1-8 was to test the possibility of reversing changes in aged Leydig cells by exogenous supplementation of thyroid hormone (TH) and/or LH to increase the testosterone-producing capacity of the Leydig cells to a level similar to that of the young. Rats have been suggested as suitable models for human aging studies (Hazzard, (1991) *Neurobiol. Aging* 12:645-649). The Brown Norway rat was chosen for this study, because this strain has been recommended as a suitable model for male reproductive aging studies (Wang et al., (1993) *Endocrinol.* 133:2773-2781 and Zirkin et al., (1993) *J. Androl.* 14:118-123).

According to previous reports (Wang et al., (1993) *Endocrinol.* 133:2773-2781 and Zirkin et al., (1993) *J. Androl.* 14:118-123), Brown Norway rats age differently than other strains of rats that have been studied to date (Mendis-Handagama & Gelber, (1995) *Tissue Cell* 27:689-699 and Ichihara et al., (1993) *Cell Tissue Res.* 271:241-255). Thus, another object of Examples 1-8 was to examine age-related changes in the interstitial components of the testis in Brown Norway rats to provide such information for this strain.

Example 1

Animals and Treatments

Male Brown Norway rats aged 3, 6, 12 (n=8 per group; 3M, 6M, and 12M, respectively), and 18 months (M) (n=32; 18M) were purchased from Harlan (Madison, Wis., United States of America). The 18M rats were divided equally into four groups (n=8 per group). Under deep inhalation anesthesia (METOFANE™; Malincroft Veterinary, Inc., Mundelein, Ill., United States of America), the four groups of 18M rats were implanted subdermally with ALZET™ mini-osmotic pumps (model 2ML4; Alza Corporation, Palo Alto, Calif., United States of America), containing saline (control), LH (24 µg/day; National Hormone and Pituitary Program, Los Angeles, Calif., United States of America), thyroxine (T4; 5 µg/day; Sigma, St. Louis, Mo., United States of America), and LH and T4 (LH+T4; two pumps, 24 mg/day of LH and 5 mg/day of T4), respectively, for 4 weeks (to 19 months [19M] of age). These doses of LH (Mendis-Handagama et al., (1998) *Tissue Cell* 30:64-73) and thyroid hormone (Ariyaratne et al., (2000) *Biol. Reprod.* 63:1115-1123) were used based on previously published studies. Rats were maintained under conditions of controlled temperature (25° C.) and lighting (14 hour/10 hour light/dark cycle) and were housed individually (one rat per cage). The animals were fed with Agway PRO-LAB™ rat formula (Agway, Syracuse, N.Y., United States of America) and water ad libitum until they were sacrificed. The animal protocol employed (No. 488) meets the guidelines of the National Institutes of Health and was approved by the University of Tennessee Animal Care and Concerns Committee.

Example 2

Administration of Saline and Hormones

Pumps were filled with either saline, LH, or T4, and were primed in saline for 3 hours before implantation so that they would deliver their contents immediately on subdermal implantation into the interscapular region. The LH+T4 rats received two pumps each, one containing LH and one containing T4; the other rats received one pump containing either saline, LH, or T4. After 4 weeks of treatment, rats were sacrificed. In addition, implanted pumps were removed and examined to verify that they had delivered their contents as expected.

Example 3

Serum Collection

Immediately after a rat was sacrificed, blood was drawn from its heart using the cardiac puncture technique, serum prepared (Mendis-Handagama & Gelber, (1995) *Tissue Cell* 27:689-699), and stored at −20° C. until assay.

Example 4

RIA for Serum LH, T4, Triiodothyronine, and Testosterone

Serum LH hormone was quantified using a commercially available rat luteinizing hormone (rLH) kit (Amersham Pharmacia Biotech, Piscataway, N.J., United States of America). The sensitivity of LH assay was 0.8 ng/ml. The interassay coefficient of variation was less than 10.97%, and the intraassay coefficient of variation was less than 6.5%. The cross-reactivity of the antibody for LH was 0.66% for rat TSH, 0.1% for rat growth hormone, less than 0.016% for rat follicle stimulating hormone (FSH), less than 0.8% for rat prolactin, and less than 0.00092% for rat adenocorticotropic hormone (ACTH). Serum T4, triiodothyronine (T3), and testosterone were assayed using commercially available kits (available under the trademark COAT-A-COUNT™ from Diagnostics Products Corp., Los Angeles, Calif., United States of America). The interassay coefficients of variation for T4, T3, and testosterone assays were less than 14.5%, 10%, and 11%, respectively. The intraassay coefficients of variation for T4, T3, and testosterone assays were less than 3.8%, 8.9%, and 9%, respectively. The antibody used in the T4 assay had 2% cross-reactivity with T3, and the antibody used in the T3 assay had less than 1% cross-reactivity with T4. The crossreactivity of the antibody used in the testosterone RIA kit was 2.8% for dihydrotestosterone, 0.5% for androstenedione, and less than 0.02% for other steroids.

Example 5

LH-Stimulated Testicular Steroidogenesis In Vitro

One testis of each rat in the 3M, 6M, 12M, and 19M age groups was removed, cleaned of fat, and weighed on a Mettler H54 balance to obtain the fresh testis weight. Using the flotation technique (Mendis-Handagama et al., (1988) *Am. J. Anat.* 181:12-22; Mori & Christensen, (1980) *J. Cell. Biol.* 84:340-354; and Mendis-Handagama & Ewing, (1990) *J. Microsc.* (Oxf) 159:73-82), the specific gravity of the fresh testis was determined as described previously (Mori & Christensen, (1980) *J. Cell. Biol.* 84:340-354 and Mendis-Handagama & Ewing, (1990) *J. Microsc.* (Oxford) 159:73-82), and the fresh testis volume was calculated by dividing the fresh testis weight by the specific gravity (in metric units, specific gravity equals density). This measurement is required to express Leydig cell numbers per testis, because numerical density is obtained as a number per unit volume of the testis. The testis was then decapsulated, and the entire testis was incubated for 3 hours in the same medium as described previously (Ariyaratne et al., (2000) *Biol. Reprod.* 63:1115-1123; Mendis-Handagama et al., (1998) *Biol. Reprod.* 59:351-357; Mendis-Handagama et al., (1990) *J. Androl.* 11:548-554; Ariyaratne et al., (2000) *Biol. Reprod.* 63:493-502; and Ariyaratne & Mendis-Handagama, (2000) *Biol. Reprod.* 62:158-168) to determine the LH-stimulated testosterone-secretory capacity per testis in vitro. Testosterone levels in the incubation medium were measured by RIA using commercially available kits (COAT-A-COUNT™), and the details of the assay are given above (see Laboratory Example 4). Testosterone-secretory capacity per Leydig cell was calculated by dividing the testosterone-secretory capacity per testis by the number of Leydig cells per testis.

Example 6

Fixation and Processing of Testis Tissue

The other testis of each rat in the 3M, 6M, 12M, and 19M age groups (n=8 per group) was fixed by whole-body perfusion (Mendis-Handagama et al., (1988) *Am. J. Anat.* 181:12-22; Mendis-Handagama et al., (1998) *Biol. Reprod.* 59:351-357; Ariyaratne et al., (2000) *Biol. Reprod.* 63:493-502; and Ariyaratne & Mendis-Handagama, (2000) *Biol. Reprod.* 62:158-168), and the fixed testis was then weighed, the specific gravity measured, and the fixed testis volume calculated. These fixed testes were processed for microscopy and stereology as described previously (Mendis-Handagama et al., (1988) *Am. J. Anat.* 181:12-22; Mendis-Handagama et al., (1998) *Biol. Reprod.* 59:351-357; Ariyaratne et al., (2000) *Biol. Reprod.* 63:493-502; and Ariyaratne & Mendis-Handagama, (2000) *Biol. Reprod.* 62:158-168). Shrinkage of testis tissue from the fresh to the processed state was determined as previously published (Mendis-Handagama & Ewing, (1990) *J. Microsc.* (Oxford) 159:73-82) for use in the stereological studies.

Example 7

Microscopy and Stereology

Two tissue sections of 1 μm in thickness and four sections apart were cut from the testis tissue blocks prepared for stereology using a LKB IV ultramicrotome and glass knives. These sections were stained with methylene blue. The volume density of testicular components, which is defined as the volume of the component per unit volume of testis tissue, was obtained via point counting as described previously (Mendis-Handagama et al., (1988) *Am. J. Anat.* 181:12-22; Mendis-Handagama et al., (1998) *Biol. Reprod.* 59:351-357; and Ariyaratne & Mendis-Handagama, (2000) *Biol. Reprod.* 62:158-168). Four corners of every tissue section (four fields/section, one section/block, and 10 blocks/rat, for a total of 40 fields/rat) were analyzed with an Olympus BH-2 light microscope. The unbiased sampling rule of Sterio (Sterio, (1984) *J. Microsc.* (Oxford) 134:127-137) was used to avoid bias and overlapping of the fields tested. The tested components included seminiferous tubules, testis interstitium, lymphatic space, Leydig cells (identified by their distinct peripheral rim of nuclear heterochromatin and abundant granular cytoplasm), blood vessels, macrophages (identified by nuclear heterochromatin and vacuolated cytoplasm, which stains differently from Leydig cells), and connective tissue cells (peritubular myoid cells, fibroblasts, endothelial cells of blood and lymph vessels, and pericytes; these cells were identified by their location and elongated, spindle-like shape). The formula used to obtain the volume density of each testicular component was as follows: volume density of component=(number of points on each component/total number of points on testis tissue)×100.

The numerical density of Leydig cells (number of cells per unit volume of testis) was obtained via the disector method, which was described by Sterio, (1984) *J. Microsc.* (Oxford) 134:127-137) and by Ariyaratne & Mendis-Handagama, (2000) *Biol. Reprod.* 62:158-168). The average volume of a Leydig cell was obtained by dividing the volume density of Leydig cells by the numerical density. Mendis-Handagama et al., (1988) *Am. J. Anat.* 181:12-22; Mendis-Handagama et al., (1998) *Biol. Reprod.* 59:351-357; and Mendis-Handagama & Ewing, (1990) *J. Microsc.* (Oxford) 159:73-82). The number of Leydig cells per testis was calculated by multiplying the numerical density by the fresh testis volume (Mendis-Handagama et al., (1988) *Am. J. Anat.* 181:12-22; Mendis-Handagama et al., (1998) *Biol. Reprod.* 59:351-357; Ariyaratne & Mendis-Handagama, (2000) *Biol. Reprod.* 62:158-168; and Sterio, (1984) *J. Microsc.* (Oxford) 134:127-137). An Olympus BH-2 light microscope was used for photography.

Example 8

Statistical Analysis

The PC SAS software (SAS Institute Inc., Cary, N.C., United States of America) was used to analyze the data. Results are expressed as mean± standard error of the mean (SEM). Significant differences (P<0.05) between the means were determined by the Duncan multiple-range test after analysis of variance (Duncan, (1975) *Biometrics* 31:339-359).

Results of Examples 1-8

The testis volumes and volume densities of testicular components are shown in Table 1. The absolute volumes of testicular components per testis are given in Table 2. The numbers of Leydig cells, macrophages, and connective tissue cells per testis and the average volume of a Leydig cell are shown in Table 3.

The absolute volume of Leydig cells per testis did not change with age advancement from 3M to 6M but was significantly reduced at 12M; a further reduction was seen at 19M (control). By contrast, all other 19M groups (i.e., LH–, T4–, and LH+T4-treated) had higher values compared to 19M control rats; however, statistical significance was not observed between 19M T4-treated and 19M control rats due to the higher SEM in the latter group. Additionally, the value of the 19M LH-treated group was not significantly different from those of the 3M and 6M groups, and the values of the 19M T4– and 19M LH+T4-treated groups were not significantly different from those of 12M rats.

The number of Leydig cells per testis (Table 3) was not significantly different among all experimental groups. The average volume of a Leydig cell (Table 3) was unchanged with age advancement from 3M to 6M; however, significant reductions were observed first in 12M rats and then in

TABLE 1

Mean Testis Volume (mm$^3$) and Volume Density of Testicular Components (%)

| Parameter | 3M | 6M | 12M | 19M Control | 19M LH | 19M T4 | 19M LH + T4 |
|---|---|---|---|---|---|---|---|
| Testis volume | 1674 | 1736 | 1683 | 1716 | 1804 | 1838 | 1783 |
|  | $(74)^a$ | $(82)^a$ | $(68)^a$ | $(56)^a$ | $(72)^a$ | $(66)^a$ | $(71)^a$ |
| Seminiferous tubules | 89.21 | 89.43 | 88.99 | 88.03 | 88.93 | 87.84 | 88.5 |
|  | $(0.66)^a$ | $(0.65)^a$ | $(0.39)^a$ | $(1.59)^a$ | $(0.41)^a$ | $(0.57)^a$ | $(0.52)^a$ |
| Interstitium | 10.80 | 10.568 | 11.013 | 11.97 | 11.066 | 12.165 | 11.5 |
|  | $(0.78)^a$ | $(0.65)^a$ | $(0.29)^a$ | $(1.64)^a$ | $(0.57)^a$ | $(0.42)^a$ | $(0.53)$ |
| Connective tissue cells | 1.40 | 1.43 | 1.39 | 1.41 | 1.29 | 1.25 | 1.29 |
|  | $(0.09)^a$ | $(0.02)^a$ | $(0.07)^a$ | $(0.17)^a$ | $(0.09)^a$ | $(0.06)^a$ | $(0.09)^a$ |
| Macrophages | 0.438 | 0.423 | 0.448 | 0.513 | 0.58 | 0.523 | 0.447 |
|  | $(0.02)^a$ | $(0.07)^a$ | $(0.07)^a$ | $(0.07)^a$ | $(0.05)^a$ | $(0.06)^a$ | $(0.03)^a$ |
| Lymphatic space | 3.92 | 3.57 | 3.98 | 4.55 | 4.09 | 5.29 | 4.65 |
|  | $(0.17)^{ab}$ | $(0.29)^b$ | $(0.47)^{ab}$ | $(0.95)^{ab}$ | $(0.54)^{ab}$ | $(0.24)^a$ | $(0.14)^{ab}$ |
| Blood vessels | 1.49 | 1.80 | 2.27 | 3.13 | 2.35 | 2.61 | 3.00 |
|  | $(0.43)^a$ | $(0.17)^b$ | $(0.24)^{bc}$ | $(0.37)^c$ | $(0.09)^{bc}$ | $(0.12)^{bc}$ | $(0.38)$ |
| Leydig cells | 3.58 | 3.35 | 2.83 | 2.33 | 2.97 | 2.38 | 3.00 |
|  | $(0.17)^a$ | $(0.14)^{ab}$ | $(0.14)^{cd}$ | $(0.13)^d$ | $(0.31)^{bc}$ | $(0.04)^d$ | $(0.02)^{bc}$ |

$^{a-d}$Numbers in parentheses are SEM. In each row, values with different superscripts are significantly different (P < 0.05).

TABLE 2

Mean Absolute Volume of Testicular Components (mm$^3$)

| Parameter | 3M | 6M | 12M | 19M Control | 19M LH | 19M T4 | 19M LH + T4 |
|---|---|---|---|---|---|---|---|
| Seminiferous tubules | 1465.65 | 1552.85 | 1497.77 | 1510.16 | 1595.38 | 1608.77 | 1556.50 |
|  | $(46.69)^a$ | $(23.93)^a$ | $(83.01)^a$ | $(57.35)^a$ | $(25.77)^a$ | $(24.63)^a$ | $(85.82)^a$ |
| Interstitium | 180.77 | 183.15 | 184.73 | 205.84 | 208.62 | 226.74 | 203.17 |
|  | $(14.45)^a$ | $(10.02)^a$ | $(7.25)^a$ | $(33.85)^a$ | $(11.29)^a$ | $(8.57)^a$ | $(35.54)^a$ |
| Connective tissue cells | 23.42 | 24.83 | 24.41 | 24.28 | 23.28 | 22.96 | 22.66 |
|  | $(1.67)^a$ | $(0.55)^a$ | $(2.05)^a$ | $(3.55)^a$ | $(1.77)^a$ | $(0.96)^a$ | $(2.22)^a$ |
| Macrophages | 7.31 | 7.32 | 7.4 | 8.86 | 10.45 | 10.58 | 7.93 |
|  | $(0.27)^a$ | $(1.17)^a$ | $(0.93)^a$ | $(1.49)^a$ | $(1.06)^a$ | $(1.17)^a$ | $(0.99)^a$ |
| Lymphaticspace | 65.73 | 61.87 | 66.76 | 78.93 | 73.78 | 97.19 | 82.91 |
|  | $(10.22)^{bc}$ | $(4.72)^c$ | $(8.01)^{bc}$ | $(19.06)^{ab}$ | $(8.71)^b$ | $(4.18)^a$ | $(16.25)^a$ |
|  |  |  |  |  |  |  | $b$ |

TABLE 2-continued

Mean Absolute Volume of Testicular Components (mm³)

| | | | | 19M | | | |
|---|---|---|---|---|---|---|---|
| Parameter | 3M | 6M | 12M | Control | LH | T4 | LH + T4 |
| Blood vessels | 19.64 | 31.17 | 38.08 | 54.12 | 42.82 | 47.97 | 53.61 |
| | $(7.11)^a$ | $(2.82)^b$ | $(4.24)^c$ | $(8.47)^d$ | $(0.750)^{ec}$ | $(1.85)^{de}$ | $(9.52)^d$ |
| Leydig cells | 59.99 | 58.14 | 47.38 | 38.22 | 50.26 | 43.57 | 45.02 |
| | $(3.19)^a$ | $(1.95)^a$ | $(2.17)^{bc}$ | $(3.69)^c$ | $(4.72)^{ab}$ | $(0.37)^{bc}$ | $(2.52)^{bc}$ |

$^{a\text{-}d}$Numbers in parentheses are SEM. In each row, values with different superscripts are significantly different (P < 0.05).

TABLE 3

Mean Cell Number per Testis (10⁶) and Average Volume of a Leydig Cell (μm³)

| | | | | 19M | | | |
|---|---|---|---|---|---|---|---|
| Parameter | 3M | 6M | 12M | Control | LH | T4 | LH + T4 |
| Leydig cell number | 24.76 | 24.64 | 24.99 | 22.53 | 24.42 | 21.80 | 22.61 |
| | $(2.3)^a$ | $(1.9)^a$ | $(2.8)^a$ | $(2.2)^a$ | $(2.6)^a$ | $(2.6)^a$ | $(2.66)^a$ |
| Macrophage number | 5.47 | 6.84 | 6.9 | 6.79 | 7.22 | 7.65 | 7.54 |
| | $(0.19)^a$ | $(0.22)^{ab}$ | $(0.42)^{ab}$ | $(0.87)^{ab}$ | $(0.87)^{bc}$ | $(0.23)^c$ | $(0.39)^c$ |
| Connective tissue cell number | 22.43 | 24.11 | 23.11 | 24.66 | 25.15 | 24.33 | 24.43 |
| | $(3.71)^a$ | $(1.43)^a$ | $(4.51)^a$ | $(3.17)^a$ | $(1.86)^a$ | $(1.52)^a$ | $(3.41)^a$ |
| Average volume of a Leydig cell | 2413 | 2173 | 1895 | 1696 | 2145 | 1998 | 2365 |
| | $(175)^a$ | $(152)^a$ | $(60)^b$ | $(47)^c$ | $(235)^{ab}$ | $(66)^b$ | $(72)^a$ |

$^{a\text{-}d}$Numbers in parentheses are SEM. In each row, values with different superscripts are significantly different (P < 0.05).

19M control rats. The average volume of a Leydig cell in 19M LH– and LH+T4-treated rats was not significantly different from those in 3M and 6M rats. This value in 19M T4-treated rats was significantly lower than those in 3M and 6M rats, although it was not significantly different from those in 19M LH-treated and 12M rats.

Figure 1B:
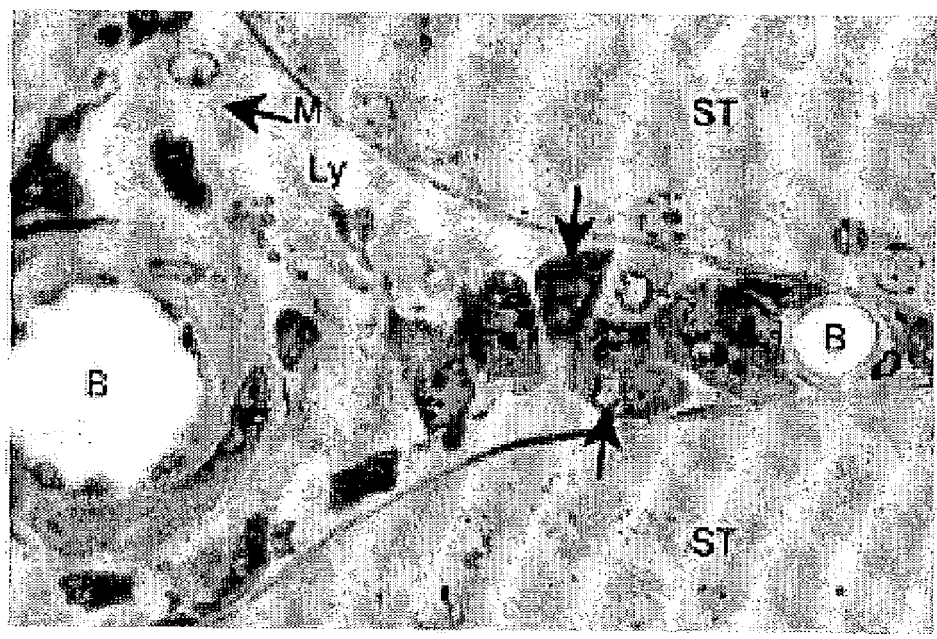
FIG. 1B is a light micrograph of testis interstitium of brown Norway rats aged 6 months. Arrows depict Leydig cells. c indicates connective tissue cells; Ly indicates lymphatic space; M indicates macrophages; ST indicates seminiferous tubules. Bar=7.7 μm, same magnification for all micrographs.
Figure 1C:
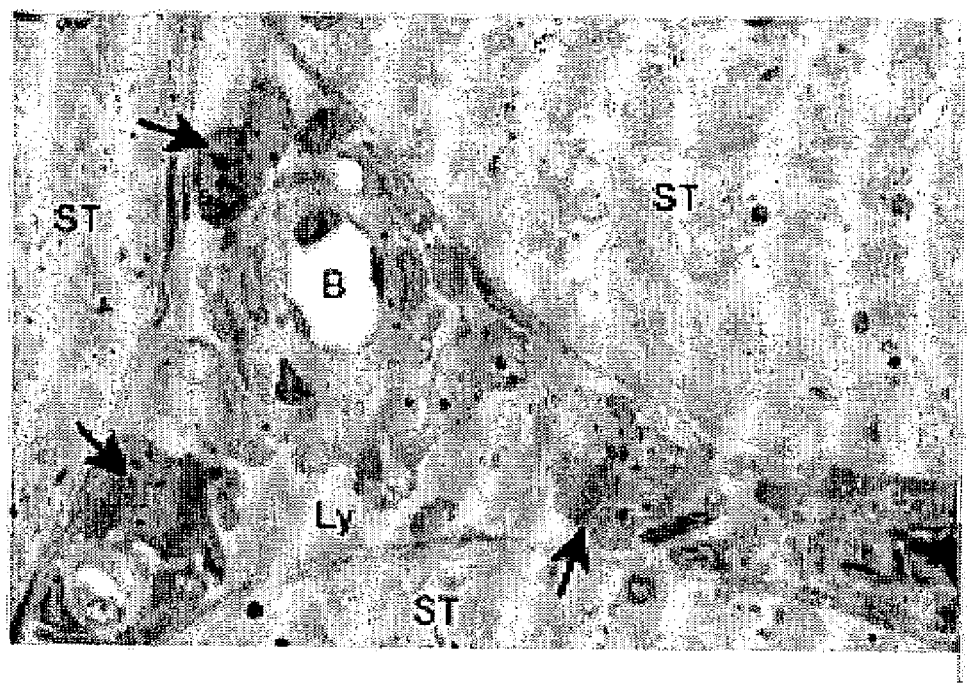
FIG. 1C is a light micrograph of testis interstitium of brown Norway rats aged 12 months. Arrows depict Leydig cells. c indicates connective tissue cells; Ly indicates lymphatic space; M indicates macrophages; ST indicates seminiferous tubules. Bar=7.7 μm, same magnification for all micrographs.
Figure 1D:
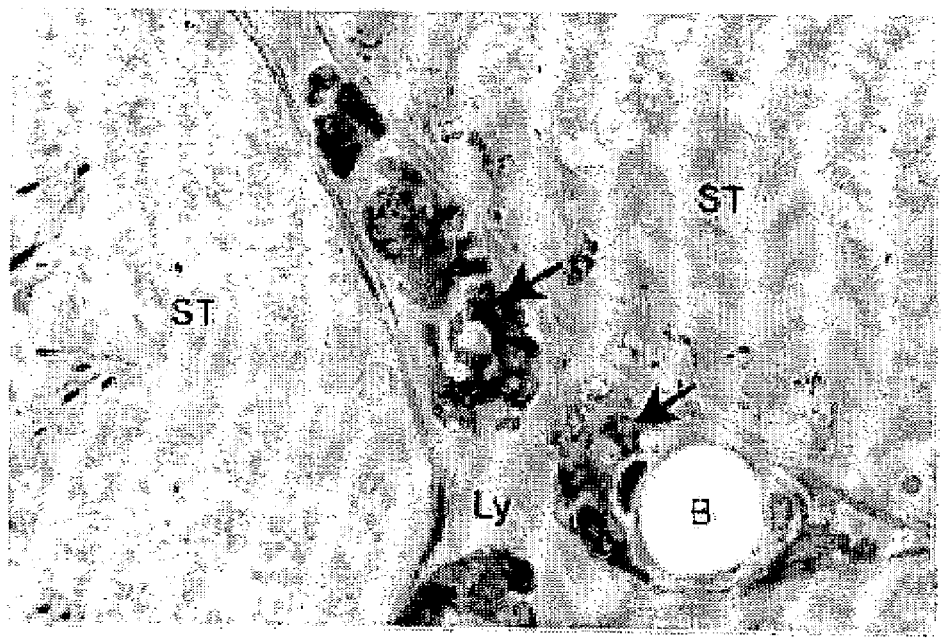
FIG. 1D is a light micrograph of testis interstitium of brown Norway rats aged 19 months and treated with saline. Arrows depict Leydig cells. c indicates connective tissue cells; Ly indicates lymphatic space; M indicates macrophages; ST indicates seminiferous tubules. Bar=7.7 μm, same magnification for all micrographs.
Figure 1E:
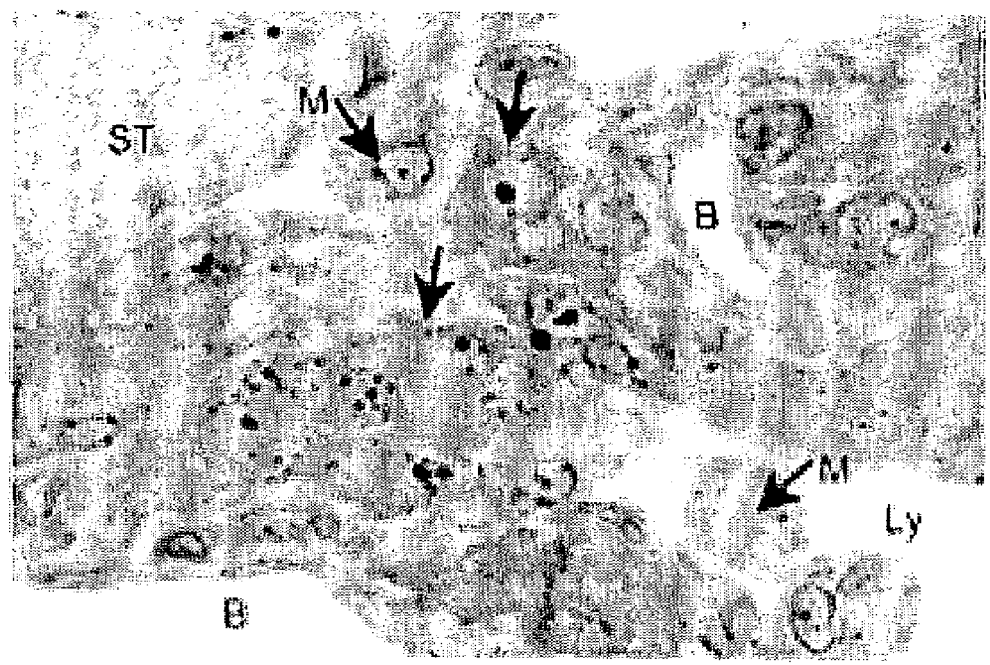
FIG. 1E is a light micrograph of testis interstitium of brown Norway rats aged 19 months and treated with LH. Arrows depict Leydig cells. c indicates connective tissue cells; Ly indicates lymphatic space; M indicates macrophages; ST indicates seminiferous tubules. Bar=7.7 µm, same magnification for all micrographs.
Figure 1F:
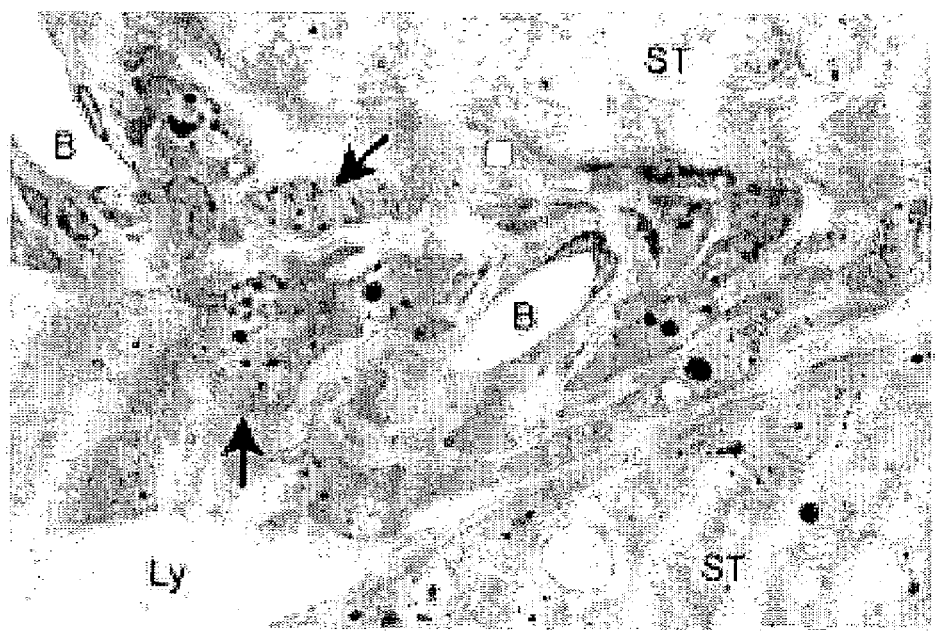
FIG. 1F is a light micrograph of testis interstitium of brown Norway rats aged 19 months and treated with T4. Arrows depict Leydig cells. c indicates connective tissue cells; Ly indicates lymphatic space; M indicates macrophages; ST indicates seminiferous tubules. Bar=7.7 µm, same magnification for all micrographs.
Figure 1G:
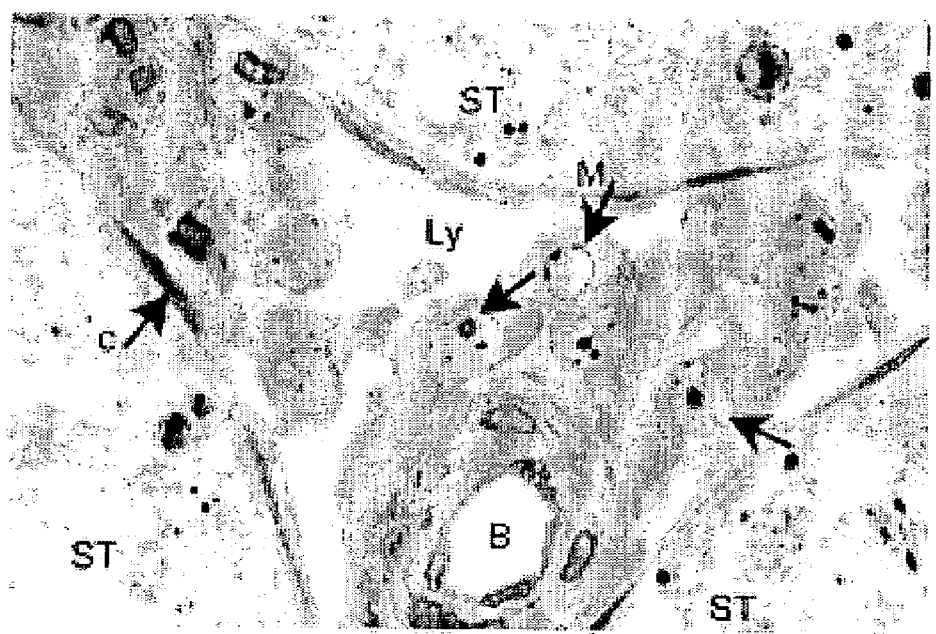
FIG. 1G is a light micrograph of testis interstitium of brown Norway rats aged 19 months and treated with LH and T4. Arrows depict Leydig cells. c indicates connective tissue cells; Ly indicates lymphatic space; M indicates macrophages; ST indicates seminiferous tubules. Bar=7.7 µm, same magnification for all micrographs.

Microscopic studies also revealed that the size of Leydig cell profiles in tissue sections progressively decreased with age (from 3M to 19M), and that these profiles in 19M LH–, T4–, and LH+T4-treated rats appeared to be much larger than those in 19M control rats (FIGS. 1A-1G). Thickening of the walls of some blood vessels, mainly due to the accumulation of connective tissue cells, was also observed occasionally in 6M and older rats (FIGS. 1A-1G); however, the amount of collagen in the testis interstitium, which usually increases with age advancement in other strains of rats, was not evident in this strain.

Table 4 shows LH-stimulated testosterone-secretory capacity per testis and per Leydig cell in vitro. No difference was observed between 3M and 6M rats for both these parameters, but significant reductions were observed in 12M and 19M control rats. Both these parameters in 19M LH+T4-treated rats were similar to those in 3M and 6M rats, and these values in 19M LH– and T4-treated rats were comparable to those in 12M rats.

Serum LH, T4, T3, and testosterone levels are shown in Table 5. As Table 5 indicates, serum LH levels were unchanged from 3M to 12M rats but were reduced significantly in 19M control and T4-treated rats compared with 3M through 12M rats. In 19M LH– and LH+T4-treated rats, LH levels were greater than those of 3M to 12M rats. Both T4 and T3 levels in serum were highest in 3M and 6M rats and lowest in 19M control rats. These hormone levels in 19M T4– and LH+T4-treated rats were similar to those in 12M rats and were higher than those in 19M LH-treated rats. Continuing with Table 5, serum testosterone levels did not change significantly from 3M to 12M rats, although the mean value in 12M rats was approximately 20% lower than those in 3M and 6M rats. The lowest value was observed in 19M control rats; the values in 19M L–, T4–, and LH+T4-treated rats were significantly greater than 19M controls. Serum testosterone levels in 19M LH– and T4–

TABLE 4

Mean Testosterone-Secretory Capacity per Testis (ng) and per Leydig Cell (pg)

| | | | | 19M | | | |
|---|---|---|---|---|---|---|---|
| Parameter | 3M | 6M | 12M | Control | LH | T4 | LH + T4 |
| Per testis | 20,653 | 19,127 | 14,481 | 10,077 | 14,753 | 14,748 | 19,283 |
| | $(4404)^a$ | $(2999)^a$ | $(2890)^b$ | $(1980)^c$ | $(1807)^b$ | $(3558)^b$ | $(2552)^a$ |
| Per Leydig cell | 0.83 | 0.77 | 0.58 | 0.45 | 0.63 | 0.67 | 0.81 |
| | $(0.06)^a$ | $(0.04)^a$ | $(0.01)^b$ | $(0.02)^c$ | $(0.02)^b$ | $(0.04)^b$ | $(0.03)^a$ |

$^{a\text{-}d}$Numbers in parentheses are SEM. In each row, values with different superscripts are significantly different (P < 0.05).

TABLE 5

Mean Serum LH, T4, T3, and Testosterone Levels

| | | | | 19M | | | |
|---|---|---|---|---|---|---|---|
| Hormones | 3M | 6M | 12M | Control | LH | T4 | LH + T4 |
| LH (ng/ml) | 34.56 (23)[b] | 34.46 (1.9)[b] | 34.99 (2.1)[b] | 27.13 (1.3)[d] | 49.43 (2.3)[a] | 30.28 (1.1)[c] | 47.16 (2.6)[a] |
| T4 (ng/dl) | 4.08 (0.141)[a] | 4.11 (0.111)[a] | 3.03 (0.012)[b] | 1.61 (0.101)[d] | 2.03 (0.106)[c] | 2.98 (0.052)[b] | 2.87 (0.171)[b] |
| T3 (ng/dl) | 86.12 (1.5)[a] | 87.01 (1.2)[a] | 64.35 (2.3)[b] | 48.16 (1.7)[d] | 56.11 (2.5)[c] | 66.62 (2.6)[b] | 65.65 (1.7)[b] |
| Testosterone (ng/dl) | 223.6 (63.8)[a] | 233.1 (51.3)[a] | 181.5 (72.2)[ae] | 52.1 (9.9)[b] | 109.2 (24.7)[c] | 73 (9.44)[d] | 167.1 (16.6)[e] |

[a-d]Numbers in parentheses are SEM. In each row, values with different superscripts are significantly different (P < 0.05).

treated rats were significantly lower than those in 3M through 12M rats. Although the serum testosterone levels in 19M LH+T4-treated rats were not significantly different from those in 12M rats, they were 27% lower (P<0.05) than those in 3M and 6M rats.

Discussion of Examples 1-8

Several important findings of Examples 1-8 include the results of the treatments of aged Brown Norway rats with LH, T4, and LH+T4 regarding enhancement of the testicular steroidogenic function. It is noted that these treatments did not cause specific changes in testis volume, absolute volumes of testicular components (except for the Leydig cells), or numbers of testicular interstitial cells (including the Leydig cells). However, all three treatments were able to increase the absolute volume of Leydig cells per testis and the average volume of a Leydig cell above that of aged, 19M control rats, which had the lowest values for these parameters when compared with all the treatment groups. It is also noted that separate treatment with LH or T4 could improve the testicular steroidogenic potential in vitro to that of 12M rats, and that the combined treatment (LH+T4) was effective in upgrading this potential to those of 3M and 6M rats. Although it is not the inventor's desire to be bound by any theory of operation, it is hypothesized that these findings suggest that changes in the circulating levels of LH and T4 are the major factors responsible for Leydig cell hypotrophy and loss in their steroidogenic potential with aging, direct, and/or indirect effects of other hormones and factors on Leydig cells that could be associated with these age-related changes are not ruled out.

The rats treated with LH+T4 upgraded the steroidogenic potential of Leydig cells in vitro to those of 3M and 6M rats. The serum testosterone levels of the LH+T4 treat rats were raised only to the level of 12M rats (i.e., 73% recovery compared to 3M rats). However, this enhancement is more than 300% compared to 19M control rats. Among the possibilities for the lower serum testosterone levels in LH+T4-treated rats, two that are possible include the very high levels of serum LH and the less-than-normal levels of T4 (compared to 3M and 6M rats). Therefore, adjustments in the doses of LH and T4 in LH+T4-treated rats allow the achievement of the desired serum testosterone levels in these aged rats.

Examples 1-8 revealed that, although T4 treatment alone was partially effective in restoring the average volume of a Leydig cell (i.e., to a level comparable with that of 12M rats), it was equally effective as the LH-only treatment in upgrading the steroidogenic potential of Leydig cells in vitro to the level of 12M rats. Additionally, T4 alone was not sufficient to upgrade the serum testosterone levels in 19M rats to those of 3M and 6M rats. It is also noted that the dose of T4 (5 µg/day) employed in the present Examples was insufficient to produce circulating T4 and T3 levels in the aged rats similar to those in 3M and 6M rats.

With LH+T4 treatment, the aged Leydig cells of 19M Brown Norway rats were rejuvenated remarkably; their average cell volume and the steroidogenic potential in vitro were completely reversed, to values similar to those of 3M and 6M rats. Although the serum testosterone levels of these rats were raised only to the level of 12M rats (i.e., 73% recovery compared to 3M rats), this was a 300% increase compared to 19M control rats. Therefore, the presently claimed subject matter can achieve the desired serum testosterone levels by adjusting the present LH and T4 doses (for example, to be lower and higher, respectively).

The results of the Examples also showed no change in the mean testis volume (approximating testis weight in metric units) in Brown Norway rats with aging, which compares favorably with previously published results of studies using this strain (Chen et al., (1994) *J. Androl.* 15:551-557 and Zirkin et al., (1993) *J. Androl.* 14:118-123). This is in contrast to observations in the Sprague-Dawley (Mendis-Handagama & Gelber, (1995) *Tissue Cell* 27:689-699) and Wistar strains (Ichihara et al., (1993) *Cell Tissue Res.* 271:241-255), which show increased testis volumes and weights with aging. In the present Examples, significant differences in testis weights and volumes between the right and left testicles was not observed in 19M Brown Norway rats, although the occurrence of small and large testes has been reported previously in 21-month-old (Chen et al., (1994) *J. Androl.* 15:551-557) as well as in 22-month-old and 30-month-old (Wang et al., (1993) *Endocrinol.* 133:2773-2781) Brown Norway rats.

Comparing these changes in Brown Norway rats with those in Sprague-Dawley and Wistar rats reveals both differences and similarities among these strains. In brief, Leydig cell hypotrophy and reduced steroidogenic capacity is also observed with aging in Sprague-Dawley (Mendis-Handagama & Gelber, (1995) *Tissue Cell* 27:689-699) and Wistar rats (Ichihara et al., (1993) *Cell Tissue Res.* 271:241-255). However, unlike in the Brown Norway rat, the number of Leydig cells per testis is increased with aging in Sprague-Dawley (Mendis-Handagama & Gelber, (1995) *Tissue Cell* 27:689-699) and Wistar rats (Ichihara et al., (1993) *Cell Tissue Res.* 271:241-255). Occurrence of Leydig cell hyperplasia in the aged testes has also been reported in stallions (Johnson & Neaves, (1981) *Biol. Reprod.* 24:703-712) and humans (Kothari & Gupta, (1974) *Int. J. Fertil.* 19:140-146).

Increased collagen deposition and thickening of the blood vessels in the testis interstitium have been described in aged Sprague-Dawley and Wistar rats (Mendis-Handagama & Gelber, (1995) *Tissue Cell* 27:689-699 and Ichihara et al., (1993) *Cell Tissue Res.* 271:241-255). By contrast, the present Examples showed that these changes were either minimal or absent in aged Brown Norway rats. Occlusion of blood vessels is observed in human testis with aging (Vermuelen et al., (1972) *J. Clin. Endocrinol. Metab.* 34:730-735) and other conditions associated with infertility (Francavilla et al., (1979) *Arch. Androl.* 2:21-30; Mendis-Handagama et al., (1990) *J. Androl.* 11:539-547; and Nasah & Cox, (1978) *Virchows. Arch. A.* 377:225-236). Although it is not the inventor's desire to be bound by any theory of operation, it is hypothesized that these findings suggest that testicular aging occurs at a slower pace in Brown Norway rats compared with all other strains of rats studied so far.

REFERENCES

The references listed below as well as all references cited in the specification are incorporated herein by reference to the extent that they supplement, explain, provide a background for or teach methodology, techniques and/or compositions employed herein.

Altschul et al., (1990) *J. Mol. Biol.* 215: 403-10
Amin & El-Sheikh, (1977) *Acta. Anat.* 98:121-129
Anderson et al., (1996) *Bone* 18:171-177%
Ariyaratne & Mendis-Handagama, (2000) *Biol. Reprod.* 62:158-168
Ariyaratne et al., (2000) *Biol. Reprod.* 63:1115-1123
Ariyaratne et al., (2000) *Biol. Reprod.* 63:493-502
Ascoli, (ed.) (1985) *Luteinizing Hormone Action and Receptors*, CRC Press, Boca Raton, Fla., United States of America
Ascoli (1985) in *The Receptors*, Conn (ed.), vol. 2, p. 368
Bartlett et al., (1989) in *Molecular Recognition: Chemical and Biological Problems* (Roberts, ed.) Royal Society of Chemistry, London, England pp 182-196
Bethea & Walker, (1979) *J. Gerontology* 34:21-27
Chen et al., (1994) *J. Androl.* 15:551-557
Chiao et al., (1999) *J. Cell Biochem.* 73(4): 554-62
Christensen & Peacock, (1980) *Biol. Reprod.* 22:383-391
Cizza et al., (1992) *Endocrinol.* 131:2672-2680
Cizza et al., (1995) *Neuroendocrinol.* 62:506-513
Cohen et al., (1990) *J. Med. Chem.* 33: 883-894
Connolly-Martin, (1991) *Method Enzymol.* 203: 587-613
Dixon, (1992) *Trends Biotechnol.* 10: 357-363
Duncan, (1975) *Biometrics* 31:339-359
Eisen et al., (1994) *Proteins* 19: 199-221
Ewing et al., (1983) *Endocrinol.* 112:1763-1769
Francavilla et al., (1979) *Arch. Androl.* 2:21-30
Gobien, *Br. J. Urol.* 78:763-768
Gooren, (1996) *Br. J. Urol.* 78:763-768
Gribskov et al., (1986) *Nucl. Acids. Res.* 14: 6745
Guyton, (1991) in: *Textbook of Medical Physiology*, (Guyton, ed.), W.B. Saunders, Philadelphia, Pa., United States of America, pp. 831-841
Harman et al., (1978) *Endocrinol.* 102:540-544
Hazzard, (1991) *Neurobiol. Aging* 12:645-649
Hollander & Hollander, (1958) *J. Clin. Endocrinol.* 18: 966-971
Hopfinger, (1985) *J. Med. Chem.* 28: 1133-1139
Ichihara et. al., (1993) *Cell Tissue Res.* 271:241-255
Johnson & Neaves, (1981) *Biol. Reprod.* 24:703-712
Kinsey et al., (1948) *Sexual Behavior in the Human Male*, W.B. Saunders, Philadelphia, Pa., United States of America
Kirschner & Coffman, (1968) *J. Clin. Invest.* 47:38-47
Kothari & Gupta, (1974) *Int. J. Fertil.* 19:140-146
Kyte & Doolittle, (1982), *J. Mol. Biol.* 157: 105-132
Liao & Azhar, (1993) *J. Steroid Biochem. Mol. Biol.* 46:39-47
Luo et al., (1996) *J. Androl.* 17:509-515
Luo et. al., (2001) *J. Androl.* 22:149-156
Manna et al., (2001) *J. Steroid Biochem. Mol. Biol.* 76:167-177
Maran et al., (2000) *Endocr. J.* 47:417-428
Mendis-Handagama, (2000) *Tissue Cell* 32:102-106
Mendis-Handagama & Ewing, (1990) *J. Microsc.* (Oxford) 159:73-82
Mendis-Handagama & Gelber, (1995) *Tissue Cell* 27:689-699
Mendis-Handagama et al., (1988) *Am. J. Anat.* 181:12-22
Mendis-Handagama et al., (1990) *J. Androl.* 11:539-547
Mendis-Handagama et al., (1990) *J. Androl.* 11:548-554
Mendis-Handagama et al., (1992) *Endocrinol.* 131:2839-2845
Mendis-Handagama et al., (1998) *Tissue Cell* 30:64-3
Mendis-Handagama et al., (1992) *Endocrinology* 131:2839-2845
Mendis-Handagama et al., (1998) *Biol. Reprod.* 59:351-357
Mendis-Handagama et al., (1998) *Tissue Cell* 30:64-73
Morales et al., (1996) *Int. J. Impotence Res.* 8:95-97
Mori & Christensen, (1980) *J. Cell. Biol.* 84:340-354
Mori et al., (1982) *J. Clin. Endocrinol. Metab.* 55:634-641
Nasah & Cox, (1978) *Virchows. Arch. A.* 377:225-236
Needleman & Wunsch, (1970) *J. Mol. Biol.* 48:443
Norman & Litwack, (1997) in: *Hormones* (Norman & Litwack, eds.), Academic Press, San Diego, Calif., United States of America, pp. 169-191
Norman et al., (1993) in: *Hormones*, Academic Press, New York, N.Y., United States of America, pp. 169-191
Norman et al., (1997) in: *Hormones*, Academic Press, New York, N.Y., United States of America
*Computer Aided Drug Design* (1989) (Perun & Propst, eds.), Marcel-Dekker, Inc., New York, N.Y., United States of America, pp. 2-4
Polderman et al., (1993) *Ann. Intern. Med.* 118:429-432
Polderman et al., (1994) *J. Clin. Endocrinol. Metab.* 79:275-281
Riegle & Meites, (1976) *Proc. Soc. Exp. Biol. Med.* 151:507-511
Riegle & Miller, (1978) in: *The Aging Reproductive System*, (Schneider, ed.) Raven Press, New York, N.Y., United States of America, pp. 159-192
Russell et al., (1992) *Endocrinol.* 131:498-508
Sambrook & Russell, (2001) *Molecular Cloning: A Laboratory Manual*, Cold Spring Harbor Laboratory Press, Cold Spring Harbor, N.Y., United States of America
Schwartz et al. (eds.), (1979), *Atlas of Protein Sequence and Structure, National Biomedical Research Foundation*, pp. 357-358
Smith & Waterman, (1981) *Adv. Appl. Math.* 2:482
Sterio, (1984) *J. Microsc.* (Oxford) 134:127-137
Stocco, (1996) in: *The Leydig Cell* (Payne & Hardy, eds.) Cache River Press, Vienna, Ill., United States of America, pp. 241-257
Strickland et al., (1985) in: *Luteinizing Hormone Action and Receptors*, (Ascoli, ed.), CRC Press, Boca Raton, Fla., United States of America
Teerds et al., (1998) *Biol. Reprod.* 59:344-350
Theeuwes & Yum, (1976) *Ann Biomed Eng.* 4(4): 343-353
Tschinke et al., (1993) *J. Med. Chem.* 36: 3863-3870
U.S. Pat. No. 3,598,122
U.S. Pat. No. 3,598,123
U.S. Pat. No. 3,731,683

U.S. Pat. No. 3,797,494
U.S. Pat. No. 4,031,894
U.S. Pat. No. 4,201,211
U.S. Pat. No. 4,286,592
U.S. Pat. No. 4,314,557
U.S. Pat. No. 4,379,454
U.S. Pat. No. 4,435,180
U.S. Pat. No. 4,554,101
U.S. Pat. No. 4,559,222
U.S. Pat. No. 4,568,343
U.S. Pat. No. 4,573,995
U.S. Pat. No. 4,588,580
U.S. Pat. No. 4,645,502
U.S. Pat. No. 4,704,282
U.S. Pat. No. 4,788,062
U.S. Pat. No. 4,816,258
U.S. Pat. No. 4,849,226
U.S. Pat. No. 4,908,027
U.S. Pat. No. 4,943,435
U.S. Pat. No. 5,004,610
U.S. Pat. No. 5,120,546
U.S. Pat. No. 5,834,228
U.S. Pat. No. 5,872,011
U.S. Pat. No. 5,985,311
U.S. Pat. No. 6,132,760
U.S. Pat. No. 6,274,165
Valenti et al., (1997) *International J. Andrology* 20(5): 279-86
Valle et al., (1985) *J. Steroid Biochem.* 23(3): 253-7
Vermeulen (1976) in: *Hypothalamus, Pituitary and Aging*, (Everitt & Burgess, eds.), Charles C. Thomas, Springfield, Ill., United States of America, pp. 458-463
Vermeulen et al., (1972) *J. Clin. Endocrinol. Metab.* 34:730-735
Wang et al., (1993) *Endocrinol.* 133:2773-2781
Waszkowycz et al., (1994) *J. Med. Chem.* 37: 3994-4002
Wellner, (1971) *Anal. Chem.* 43:597
Wetmur & Davidson, (1968) *J. Mol. Biol.* 31:349-70
Zirkin et al., (1993) *J. Androl.* 14:118-123

It will be understood that various details of the presently claimed subject matter can be changed without departing from the scope of the presently claimed subject matter. Furthermore, the foregoing description is for the purpose of illustration only, and not for the purpose of limitation.

What is claimed is:

1. A method for rejuvenating Leydig cells in an aged male rat having Leydig cells, the method comprising:
   (a) providing an aged male rat having Leydig cells, wherein the aged male rat is 18 months of age or older; and
   (b) coadministering luteinizing hormone (LH) and thyroid hormone (TH) to the rat, whereby rejuvenation of Leydig cells in the aged male rat having Leydig cells is accomplished,
   wherein rejuvenation of the Leydig cells comprises enhanced Leydig cell serum testosterone production, increased Leydig cell volume and increased Leydig cell steroidogenic potential.

2. A method of enhancing testosterone production in an aged male rat having Leydig cells, the method comprising:
   (a) providing an aged male rat having Leydig cells, wherein the aged male rat is 18 months of age or older; and
   (b) coadministering luteinizing hormone (LH) and thyroid hormone (TH) to the rat, whereby testosterone production in the aged male rat having Leydig cells is enhanced.

* * * * *

UNITED STATES PATENT AND TRADEMARK OFFICE
CERTIFICATE OF CORRECTION

| | | |
|---|---|---|
| PATENT NO. | : 7,595,056 B1 | Page 1 of 1 |
| APPLICATION NO. | : 10/449634 | |
| DATED | : September 29, 2009 | |
| INVENTOR(S) | : S. M. L. Chamindrani Mendis-Handagama | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1003 days.

Signed and Sealed this

Twenty-eighth Day of September, 2010

David J. Kappos
*Director of the United States Patent and Trademark Office*